US010120977B2

(12) United States Patent
Coney

(10) Patent No.: US 10,120,977 B2
(45) Date of Patent: Nov. 6, 2018

(54) SECURE HEALTHCARE MANAGEMENT AND COMMUNICATION SYSTEM

(71) Applicant: BRUCE CORPORATION, Beaumont, TX (US)

(72) Inventor: Lillie Bruce Coney, Beaumont, TX (US)

(73) Assignee: BRUCE CORPORATION, Beaumont, TX (US)

( * ) Notice: Subject to any disclaimer, the term of this patent is extended or adjusted under 35 U.S.C. 154(b) by 637 days.

(21) Appl. No.: 14/648,612

(22) PCT Filed: Dec. 17, 2013

(86) PCT No.: PCT/US2013/075860
§ 371 (c)(1),
(2) Date: May 29, 2015

(87) PCT Pub. No.: WO2014/100036
PCT Pub. Date: Jun. 26, 2014

(65) Prior Publication Data
US 2015/0310173 A1 Oct. 29, 2015

Related U.S. Application Data

(60) Provisional application No. 61/738,919, filed on Dec. 18, 2012.

(51) Int. Cl.
*G06F 19/00* (2018.01)
*G06F 21/62* (2013.01)
(Continued)

(52) U.S. Cl.
CPC ........ *G06F 19/322* (2013.01); *G06F 19/3418* (2013.01); *G06F 21/6245* (2013.01);
(Continued)

(58) Field of Classification Search
CPC . G06F 19/322; G06F 19/3418; G06F 21/6245
See application file for complete search history.

(56) References Cited

U.S. PATENT DOCUMENTS 5,101,476 A 3/1992 Kukla
5,757,916 A 5/1998 MacDoran
(Continued)

FOREIGN PATENT DOCUMENTS

| CN | 101896914 | 11/2010 |
| CN | 105993157 | 10/2016 |
| WO | 2015155495 | 10/2015 |

OTHER PUBLICATIONS

Michael J. Covington et al.; "Securing Context-Aware Applications Using Environment Roles"; Georgia Institute of Technology; Atlanta, Georgia; May 2001; 11 pages.
(Continued)

*Primary Examiner* — Neal Sereboff
(74) *Attorney, Agent, or Firm* — FisherBroyles LLP; Micah Stolowitz

(57) ABSTRACT

A healthcare management and communication system including a central server, home base devices, and portable medical assistant devices (PMAD) providing secure electronic communications among medical facilities and healthcare providers, while ensuring privacy of patient medical records. In an embodiment, the central server communicates with the home base device(s) and the PMAD providing information necessary for a healthcare provider to perform a procedure for a patient. The healthcare communication system provides security for patient information by allowing the healthcare provider to access some basic patient information on the PMAD, including directions to the patient's house, when the PMAD is in all locations. Only when the PMAD is within a physical proximity to a selected home base device can the healthcare provider access the corre-
(Continued)

sponding patient's confidential information necessary for the on-site visit. Notes and data recorded during the procedure may be securely transmitted to the central server, updating the patient's record.

7 Claims, 12 Drawing Sheets

(51) Int. Cl.
  *H04L 29/06*   (2006.01)
  *G16H 10/60*   (2018.01)
(52) U.S. Cl.
  CPC .............. *G16H 10/60* (2018.01); *H04L 63/04* (2013.01); *H04L 63/0428* (2013.01)

(56) References Cited

U.S. PATENT DOCUMENTS

| | | |
|---|---|---|
| 6,336,900 B1 | 1/2002 | Alleckson |
| 6,381,577 B1 | 4/2002 | Brown |
| 6,402,691 B1 | 6/2002 | Mendard |
| 7,088,233 B2 | 8/2006 | Mendard |
| 7,142,167 B2 | 11/2006 | Rochelle |
| 7,148,791 B2 | 12/2006 | Grisham |
| 7,353,179 B2 | 4/2008 | Ott |
| 7,656,291 B2 | 2/2010 | Rochelle |
| 7,786,876 B2 | 8/2010 | Troxler |
| 8,018,329 B2 | 9/2011 | Morgan |
| 8,255,238 B2 | 8/2012 | Powell |
| 8,258,965 B2 | 9/2012 | Reeder |
| 8,320,931 B2 | 11/2012 | Ward |
| 8,508,336 B2 | 8/2013 | Giobbi |
| 8,509,806 B2 | 8/2013 | West |
| 8,581,712 B2 | 11/2013 | Morgan |
| 8,740,790 B2 | 6/2014 | Iliff |
| 8,894,577 B2 | 11/2014 | Reed |
| 9,015,008 B2 | 4/2015 | Geva |
| 9,113,300 B2 | 8/2015 | Marti |
| 9,119,034 B2 | 8/2015 | Meredith |
| 9,285,484 B2 | 3/2016 | Shima |
| 9,299,102 B1 | 3/2016 | Pike |
| 9,473,890 B1 | 10/2016 | Liu |
| 9,503,902 B1 | 11/2016 | Coney |
| 9,526,920 B2* | 12/2016 | Tanis .................. A61N 7/00 |
| 9,538,329 B1 | 1/2017 | Vivathana |
| 9,565,523 B1 | 2/2017 | Steger |
| 2004/0233930 A1* | 11/2004 | Colby, Jr. ............ G06F 1/1632 370/464 |
| 2006/0017563 A1 | 1/2006 | Rosenfeld |
| 2006/0154642 A1* | 7/2006 | Scannell, Jr. ............ A01G 9/02 455/404.1 |
| 2006/0181424 A1 | 8/2006 | Graves |
| 2006/0183980 A1 | 8/2006 | Yang |
| 2006/0277075 A1 | 12/2006 | Salwan |
| 2006/0288095 A1 | 12/2006 | Torok |
| 2007/0004971 A1* | 1/2007 | Riley .................. A61B 5/0022 600/300 |
| 2007/0213600 A1* | 9/2007 | John .................. A61B 5/0031 600/300 |
| 2008/0129496 A1* | 6/2008 | Koblasz .............. G06F 19/3462 340/540 |
| 2008/0262867 A1 | 10/2008 | Bayne |
| 2009/0206992 A1 | 8/2009 | Giobbi |
| 2009/0299770 A1 | 12/2009 | Martinez |
| 2011/0202371 A1 | 8/2011 | Darguesse |
| 2011/0221568 A1 | 9/2011 | Giobbi |
| 2011/0270640 A1* | 11/2011 | Young ................ G06Q 10/0631 705/7.12 |
| 2012/0172050 A1 | 7/2012 | Ledlie |
| 2013/0060167 A1* | 3/2013 | Dracup .................. A61B 5/11 600/595 |
| 2013/0064358 A1* | 3/2013 | Nusbaum .......... H04M 3/42068 379/88.16 |
| 2013/0072226 A1 | 3/2013 | Thramann |
| 2013/0217332 A1 | 8/2013 | Altman |
| 2013/0253700 A1* | 9/2013 | Carson .................... G07F 9/006 700/236 |
| 2013/0316645 A1 | 11/2013 | Li |
| 2013/0331118 A1 | 12/2013 | Chhabra |
| 2013/0332197 A1 | 12/2013 | Hinkel |
| 2014/0122396 A1 | 5/2014 | Swaminathan |
| 2014/0201075 A1 | 7/2014 | King |
| 2014/0278545 A1 | 9/2014 | Andrews |
| 2014/0371617 A1 | 12/2014 | Muradia |
| 2014/0379368 A1 | 12/2014 | Kim et al. |
| 2015/0201306 A1 | 7/2015 | Kazemi |
| 2016/0077186 A1 | 3/2016 | Snapp |
| 2016/0147968 A1 | 5/2016 | Coney |
| 2016/0217519 A1 | 7/2016 | Kozat |
| 2016/0381543 A1 | 12/2016 | Zhang |
| 2017/0041315 A1 | 2/2017 | Giobbi |
| 2017/0099584 A1 | 4/2017 | Bhanot |

OTHER PUBLICATIONS

Michael J. Covington et al.; A Context Aware Security Architecture for Emerging Applications; Georgia Institute of Technology; 6th ACM Symposium on Access Control Models and Technologies; Chantilly, Virginia, May 2001; 10 pages.

Indrakshi Ray et al; "A Location-Aware Role-Based Access Control Model"; Second International Conference ICISS; Kolkata, India; Dec. 2006; 15 pages.

Geetanjali Sampemane et al.; "Access Control for Active Spaces"; Department of Computer Science, University of Illinois at Urbana-Champaign; ACSAC '02 Proceedings of the 18th Annual Computer Security Applications Conference; Las Vegas, NV; Dec. 2002; 10 pages.

Urs Hengartner et al.; "Access Control to People Location Information"; University of Waterloo, Ontario, CA; ACM Transactions on Information and System Security; vol. 8 Issue 4, Nov. 2005; New York, NY; 30 pages.

Elisa Bertino et al; "A Spatially Aware RBAC"; SACMAT '05 Proceedings of the 10th ACM Symposium on Access Control Models and Technologies; Stockholm Sweden; Jun. 2005; 37 pages.

Denning and MacDoran; "Location-Based Authentication: Grounding Cyberspace for Better Security"; Computer Fraud and Security, Feb. 1996; Elsevier Science Ltd; pp. 12-16.

United States Patent and Trademark Office; International Search Report and Written Opinion PCT/US2013/0750860; dated Mar. 31, 2014, 12 Pages.

* cited by examiner

SECURE HEALTHCARE MANAGEMENT AND COMMUNICATION SYSTEM

RELATED APPLICATIONS

This application is a national stage application of international application PCT/US2013/075860, filed Dec. 17, 2013, which, in turn is a non-provisional of and claims priority benefit to U.S. Provisional application No. 61/738,919, filed Dec. 18, 2012, incorporated herein by this reference.

COPYRIGHT NOTICE

© 2012-2013 Lillie Coney. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

TECHNICAL FIELD

This invention pertains to healthcare and more specifically relates to improving delivery of healthcare services while protecting patient privacy.

BACKGROUND

Medical professionals once visited patients in their homes. As the number of patients needing treatment grew, it became more difficult for doctors or nurses to sit with sick patients in their homes. Advances in medicine, such as the development of pharmacology, better means of capturing medical knowledge to pass to future generations, specialization over general medical practices, and innovations in medical technology focusing on larger equipment requiring a specialist to operate in physically limited areas (hospitals or testing facilities), have further accelerated the shift from homecare to hospital care or in-facility treatment.

Due to the growth in the number of patients needing treatment, there are insufficient numbers of general practitioners as well as insufficient numbers of specialized doctors to serve the entire population. This problem is further complicated by the concentration of medical professionals in urban and suburban areas and the lack of medical professionals with specialized expertise in rural and certain urban areas. There are also challenges related to a medical professional's training keeping pace with the advancement of medical knowledge since, as medical professionals grow older and, in most cases, busier with patient case loads and administrative duties, it becomes more difficult for them to acquire new knowledge or learn new skills.

The shortage of qualified doctors has resulted in much of the patient interaction to be delegated to nurses, nurse practitioners, or homecare providers. Physicians and hospital administrators are well aware that they are not privy to what actually transpires with respect to interactions and treatment of patients outside their facilities. They must rely upon an elaborate model based on the physical collection of data through written notes, based upon the observations of the medical subordinate professionals who are responsible for the care of patients when the doctor is not present. This is an imperfect process for completely capturing the medical history of a patient post-hospitalization, or for patients with chronic conditions.

Managing or preventing chronic medical conditions will be the challenge of the next generation. Medical conditions do exist outside the presence of the medical profession, and efficiently and accurately monitoring changes in the medical condition of a patient outside the presence of a medical professional is an ongoing process that has not been addressed.

An efficient system for medical professionals to monitor and be informed of the results of delegated procedures will become an essential tool to medical professionals who are now in a transformative stage where they must manage larger patient caseloads, supervise more subordinate medical staff, meet the requirements of recordkeeping by government oversight agencies, and, for the well-being of their patients, supervise subordinate medical staff through oversight, management, review, and assessment.

There remains a need for providing effective and efficient care in a number of settings without requiring the presence of a physician, while still assuring patient medical privacy and keeping the primary physician informed. The person or caregiver who visits patients may or may not have extensive medical training but must provide the first line of care for patients once the doctors' initial procedures are completed. For this reason, knowing as much as possible about what is happening to a patient, and capturing data that may be critical to emergency room personnel, physicians' offices, or nurses, will be vital.

SUMMARY OF PREFERRED EMBODIMENTS

The following is a summary of the present disclosure in order to provide a basic understanding of some aspects of the disclosure. This summary is not intended to identify key/critical elements of the disclosure or to delineate the scope of the disclosure. Its sole purpose is to present some concepts of the disclosure in a simplified form as a prelude to the more detailed description that is presented later.

This disclosure describes methods and apparatus of a healthcare system for transmitting secure electronic communications and patient information among medical facilities and a healthcare provider. This may be achieved through, but is not limited to, the use of a central server for storing and transmitting information associated with a procedure to be performed by a healthcare provider, a home base device for enabling communication between a plurality of authorized devices within a selected physical proximity, and a portable medical assistant device for accessing and displaying received information associated with a procedure for a patient.

The central server may act as storage unit for a patient's health information and securely transmit a portion of the patient's health information associated with a procedure to be performed by a healthcare professional. A physician, or other medical facility staff, may assign a particular procedure to a specific healthcare professional to be performed for a patient. The central server may provide information and a selected portion of the patient's health record to one or both of the home base device and the portable medical assistant device. In an embodiment, the information provided by the central server may comprise a prescription or other instructions for administration of an examination, test, treatment or other services to a patient. The portion of the patient's health record that is relevant to the services may be transmitted as well.

Electronic communications with authorized devices may be enabled within a selected physical proximity to the home base device. In one embodiment, the home base device may operate only at two locations, adjacent the central server and at a location where the home base device is installed after installation of the home base device, as further explained below.

A portable medical assistant device may receive information associated with a patient and display the information on the device. The portable medical assistant device may have wireless networking capability, and communicate with the central server and a home base device. A selected portion of the information received by the portable medical assistant device may be displayed regardless of the location of the portable medical assistant device, while another portion of the information may only be displayed when the portable medical assistant device is within the selected physical proximity to the home base device. These features, and others below, support privacy of the patient's record notwithstanding the delivery of some healthcare procedures to the patient at a location away from the physician or hospital.

Additional aspects and advantages of this disclosure will be apparent from the following detailed description of preferred embodiments, which proceeds with reference to the accompanying drawings.

DETAILED DESCRIPTION OF PREFERRED EMBODIMENTS

This disclosure comprises a unique application of technology and protocols by medical health care providers to promote minimization of medical errors, stronger patient privacy, and greater medical care provider control over the services provided to patients in medical facilities and in home settings, assisted living, etc. One advantage is to better accommodate the growing demand for treatment options with the desire to protect and promote excellent patient outcomes-including recovery, privacy, and continuity of care. Patient privacy may rest on control of access to their medical information. The health data collection and records keeping system disclosed herein helps assure that only those authorized to create, access, or amend patient records are permitted to do so.

Figure 1A:
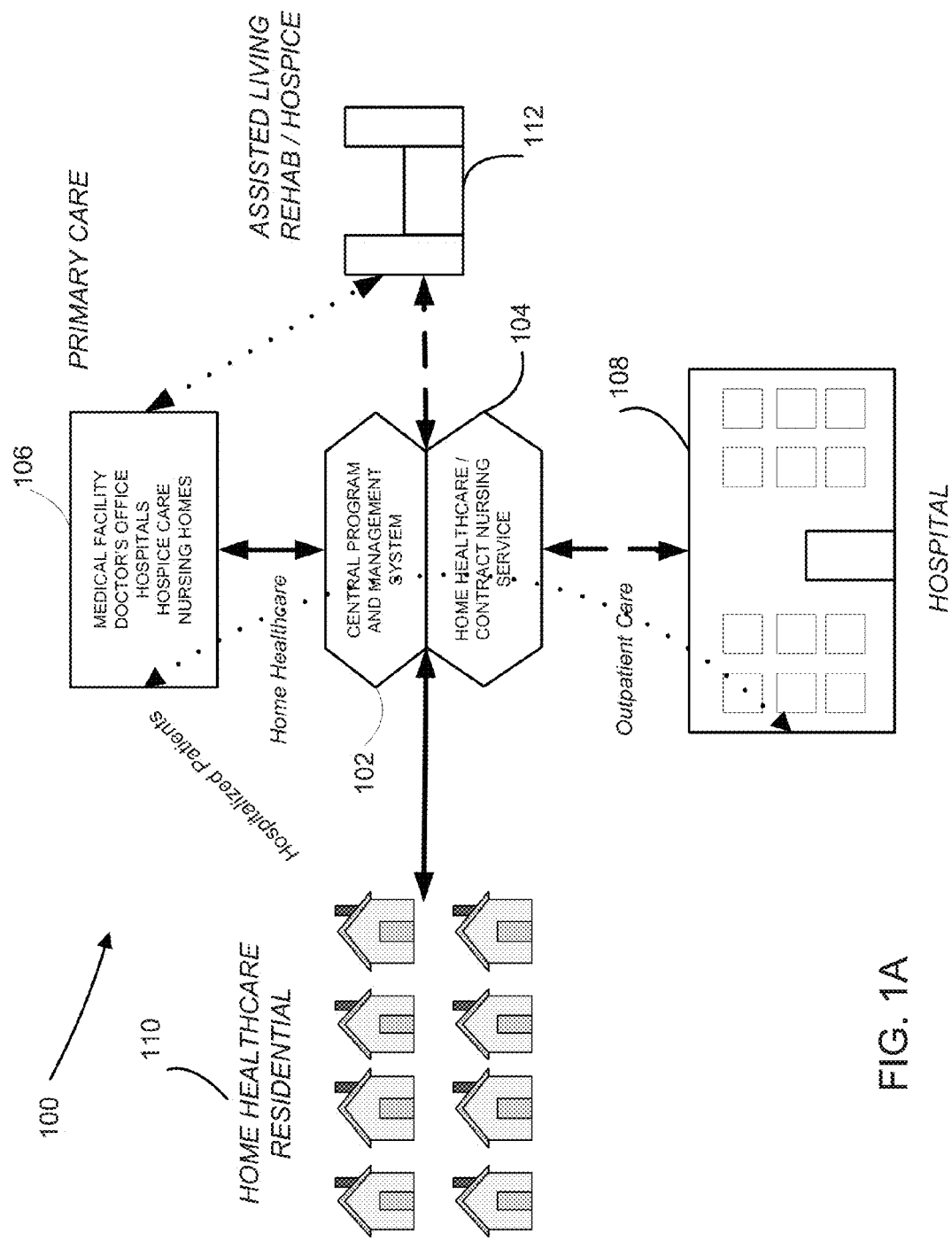
FIG. 1A is a simplified exemplary block diagram illustrating a central program and management system's service relationships with multiple facilities.

FIG. 1A is a simplified exemplary block diagram illustrating a central program and management system (CPMS) 102 service relationships with multiple facilities. The CPMS 102 may alternatively comprise a home healthcare/contract nursing service 104. The CPMS 102 may be owned and operated by medical facilities, including hospitals or physician's offices. The home healthcare/contract nursing service 104 may be owned and operated by a third-party managed service, including private nursing services. The central program and management system 102 and home healthcare/contract nursing service 104 may collectively or alternatively be referred to as the CPMS 102. For example, in an embodiment, the functionality of the CPMS may be implemented in or by a home healthcare/contract nursing service 104.

In an embodiment, a CPMS 102 may be a centralized, fixed computing device or logical server that receives requests from physicians or their designees to assign services or treatments for patients to be provided by homecare providers, therapists, or other providers. The CPMS 102 may provide adequate securing of a remote computing system that may be the foundation for creating a link between doctors, hospitals, home health care providers, and patients.

The CPMS 102 may act as a communication link among those engaged in homecare service provided to patients. The CPMS 102 may be responsible for enrolling new medical facilities (doctor's offices, hospitals, hospice care facilities, and nursing homes), and allowing the selection of home health care providers that may provide services to patients. Preferably, a CPMS supports secure near real-time communication among primary care facilities or doctors, homecare providers, and healthcare patients. In some aspects, the CPMS may be configured for logging of data for new and existing healthcare patients, engaging patients, managing visits, facilitating direct communication with authorized medical professionals, and supporting scoring (e.g. patient surveys, communication with primary medical professionals, overall patient outcomes) of home health care visits to better inform medical professionals on the effectiveness of the home treatments provided.

In an embodiment, the CPMS 102 may store a patient's medical record for only a limited period of time. At the end of the limited period of time, the patient's medical record may be pushed to a repository that is managed by a medical professional or medical facility. For example, patient record data may be held only during a period when services are being provided to the patient using the system, thereby limiting the opportunity for the confidential patient information to be disclosed.

Once the patient's medical record is pushed to the repository, the medical record may be deleted from the CPMS 102 and may not be recoverable, preventing access to confidential patient information on the PMAD (402 of FIG. 4) after the data has been transferred to CPMS. Preferably, a medical record may be deleted in such a way that it may not be reconstructed, that it does not damage the sectors on the computer server or computer's drive, or as efficiently as possible to minimize the type of damage that can happen when memories are overwritten repeatedly. Means or methods for deleting the medical record in a way that may not be reconstructed may require overwriting the medical record in memory. The process may not cause additional secondary problems with the memory may be used. This may make the CPMS 102 unattractive to external threats, attempts to breach, and prevent vulnerability to insider threats since the data retained on the CPMS 102 may not be valuable for theft and the security features may be sufficiently incorporated to effectively protect the data from misuse and abuse. In some cases, the CPMS 102 or some or all of its data storage capacity may be provisioned in remote, third-party facilities (aka "the Cloud"). In such cases, suitable agreements must be in force to ensure data security and destruction when directed.

In one embodiment, the CPMS 102 may be configured to facilitate secure communication among medical facilities 106 and home healthcare residential locations 110, as illustrated by the solid lines in 100, such that confidential medical information may not be accessed by unauthorized individuals during transmission of the information. The medical facilities 106 may comprise one or more medical facilities, doctor's offices, hospitals, hospice care facilities, nursing homes, or other facilities that may store a patient's medical record.

In other embodiments, additional or alternative communication links may be provided by the CPMS 102, as illustrated by non-solid lines in 100, allowing the CPMS 102 to service multiple facilities. These communication links may include links among the CPMS 102 and hospitals 108, among the CPMS and assisted living rehab/hospice 112, and other similar communication links.

In further embodiments, there may exist a flow of patients and/or a movement of medical records among facilities, as illustrated by dotted lines in 100. As illustrated in 100, the flow of patients and/or medical records may flow (a) between the medical facilities 106 and the hospitals 108; (b) between the medical facilities 106 and an assisted living rehab/hospice 112; and/or (c) between the CPMS and hospital 108 or other similar flows of patients and/or medical records. These flows are described further below with regard to the processes of 500 and 600.

Figure 1B:
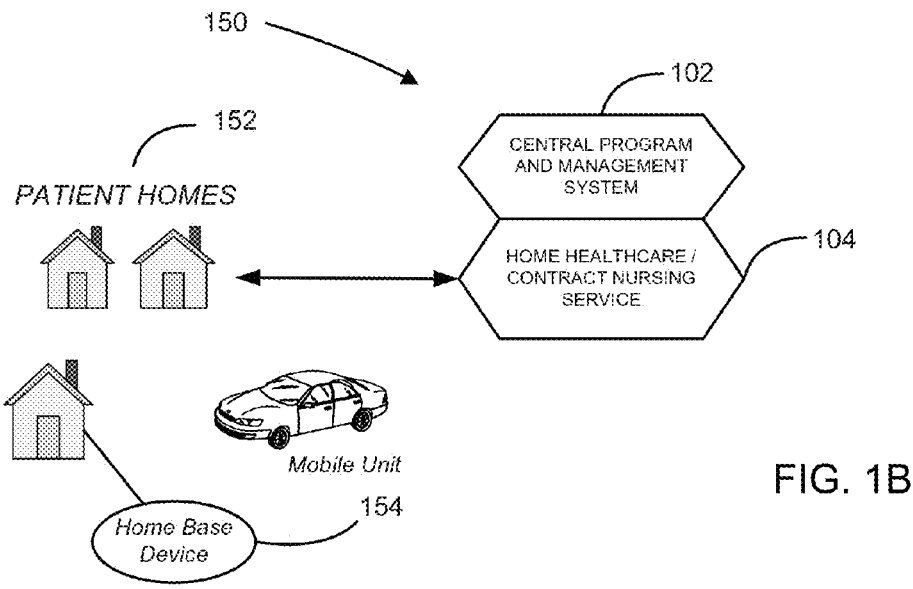
FIG. 1B is a simplified exemplary block diagram illustrating a secure system for managing healthcare service delivery in a patient's home.

FIG. 1B is a simplified exemplary block diagram illustrating a system for managing healthcare service delivery in a patient's home. A communication link may be made among patient homes 152 and the CPMS 102 or among patient homes 152 and a home healthcare/contract nursing service 104.

A home base device (HBD) 154 may be placed in a patient's home among the patient homes 152. The HBD 154 may be placed anywhere in the patient's home where it may communicate with a portable medical assistant device (PMAD) (402 of FIG. 4), such that the device may be placed in a discrete location. Placing the device in a discrete location may prevent visitors to recognizing that the patient has a condition or what the condition may be.

The HBD 154 may operate as one end of the communication link between the CPMS 102 and the patient's home. The HBD 154 preferably is configured to communicate with three types of devices: the CPMS 102, the PMAD (402 of FIG. 4), and medical assistive devices (304 of FIG. 3). The HBD 154 may assure that only the medical information necessary for a specific treatment or therapy is accessed by the PMAD (402 of FIG. 4).

The HBD 154 may require initialization and HBD 154 may wirelessly communicate with the CPMS 102 about its state to activate and run in a fixed geographic location. The HBD 154 may have its own unique IP address information and/or its own unique MAC address information. In one embodiment, the HBD 154 may operate at only two fixed locations: the location of the CPMS 102 and the location where the HBD 154 is initialized. Location may be determined by GPS, Bluetooth® short-range wireless ad hoc network, wireless telecommunication network, or other means now known or later developed.

Figure 2:
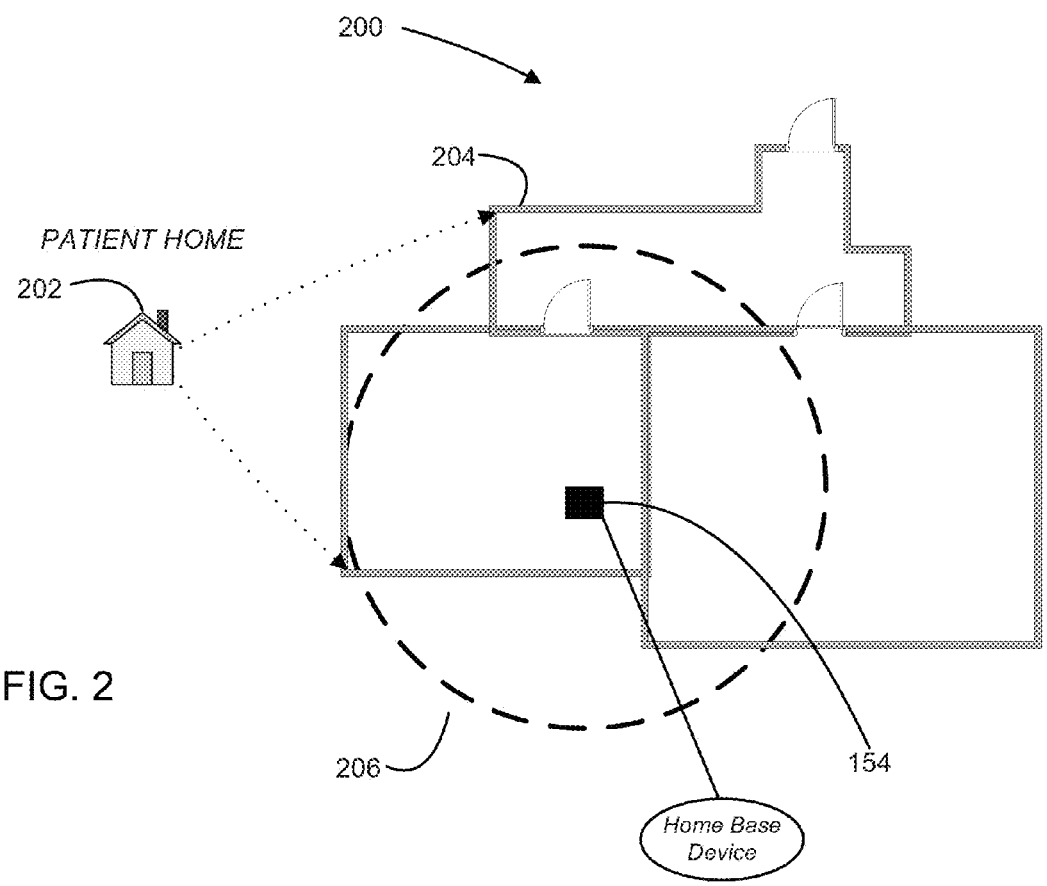
FIG. 2 illustrates an example of a proximity activation border of a home base device in an exemplary home setting.

FIG. 2 illustrates an example of a proximity activation border 206 of a HBD 154 in an exemplary home setting. A floor layout 204 of a patient's home 202 is illustrated with a HBD 154 installed. A proximity activation border 206 may be limited to a selected physical proximity from a HBD 154, therefore preventing access of confidential patient information on the PMAD (402 of FIG. 4) elsewhere.

The proximity activation border 206 may be used to enable access to a portion of information stored on a PMAD (402 of FIG. 4) when the PMAD (402 of FIG. 4) is located physically within the proximity activation border 206. Conversely, the PMAD should be configured to disallow access to selected information, for example, patient health records, when the PMAD (402 of FIG. 4) is located outside of the proximity activation border. For example, patients' records may be stored in the PMAD (402 of FIG. 4) by the CPMS 102, and secured there, so they are inaccessible unless and until the PMAD (402 of FIG. 4) is carried to a location within the defined proximity activation border 206, limiting the opportunity to misappropriate the patient's confidential information to the confines of the proximity activation border 206. Thus, for example, a healthcare provider may carry the PMAD (402 of FIG. 4) with her to a patient's home to provide assigned services. While the PMAD (402 of FIG. 4) is at the healthcare provider's home, or in her car, or elsewhere, the patient record is secure. Only after arrival at the patient's home (inside the proximity activation border 206) is the record accessible on the PMAD (402 of FIG. 4). Further, patient record updates entered by the healthcare provider will be secured as the device leaves the premises. The proximity activation border 206 may also allow communication among the HBD 154, the medical assistive devices 304, and the environment sensors 306 within the proximity activation border 206 as further described below.

Figure 3:
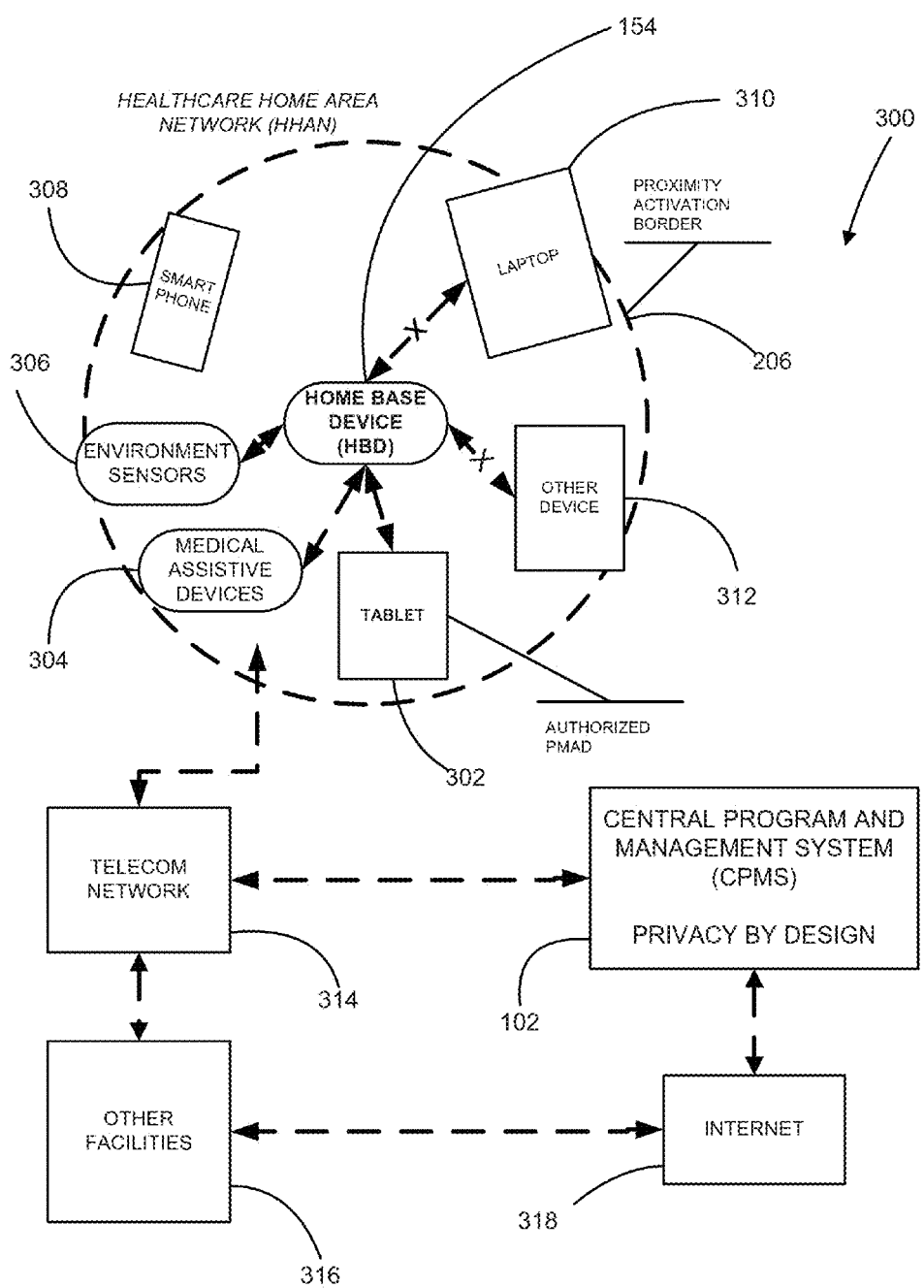
FIG. 3 is an exemplary block diagram illustrating communications among a central program and management system, a home base device, a portable medical assistant device and medical assistive devices.

FIG. 3 is an exemplary block diagram illustrating communications among a CPMS 102, a HBD 154, a PMAD (402 of FIG. 4), and medical assistive devices 304. Communication may be two-way among the devices when the devices are located within the proximity activation border 206 of the HBD 154. The HBD 154 may be configured for one-way communication to receive input from linked devices, which may comprise, for example, environment sensors 306, medical assistive devices 304, and other devices 312 associated with a patient. In this way, the HBD 154 can be used to collect data at various times, even in the absence of a healthcare provider. It can upload collected data to the CPMS 102 when available.

Figure 4:
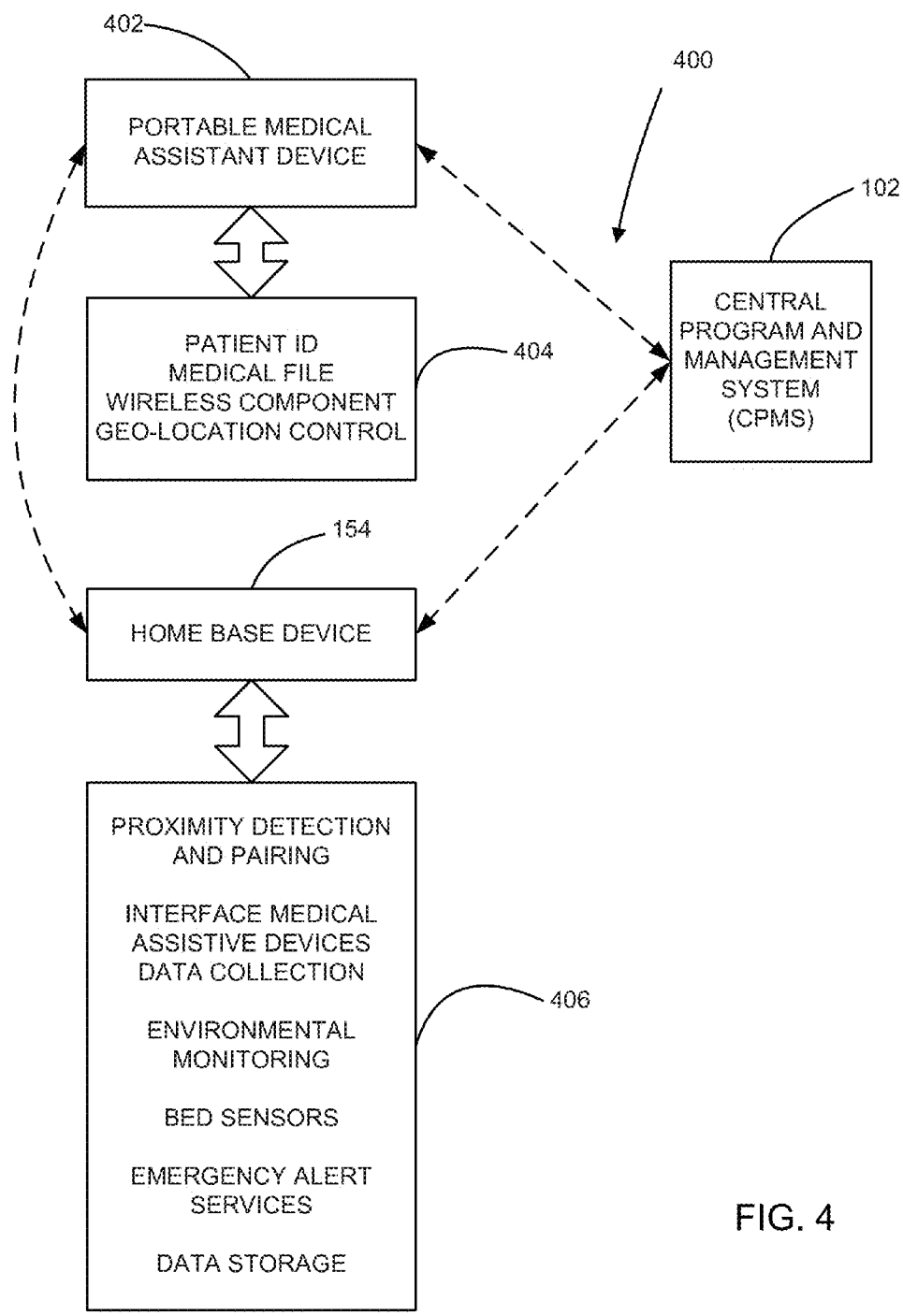
FIG. 4 is an exemplary block diagram illustrating data communication between a central program and management system, a portable medical assistant device, and a home base device.

FIG. 3 illustrates one embodiment where a tablet computer 302 may be used as the authorized PMAD (402 of FIG. 4). This may be realized by having a suitable application program installed on the tablet. The tablet, in some cases, may also provide wireless telecommunications. The installed app may limit functionality of the tablet outside of the proximity activation border 206, such as to protect against unauthorized access of a patient's confidential information. The authorized PMAD (402 of FIG. 4) is a device that may be issued to a healthcare provider or other user assigned to provide a service for a patient. The authorized PMAD (402 of FIG. 4) may also be required to meet certain credentials for communication.

The HBD 154 may be configured to communicate with the tablet 302, acting as the authorized PMAD (402 of FIG. 4), the medical assistive devices 304, and the environment sensors 306, as shown by broken lines in 300, when the devices are located within the proximity activation border 206. The HBD 154 may be further configured to not communicate with devices within the proximity activation border that are not the authorized PMAD (402 of FIG. 4), the medical assistive devices 304, and the environment sensors 306, such that unauthorized devices may not be able to access a patient's confidential information. By way of example, laptop 310 and other device 312 illustrated in 300 may not communicate with the HBD 154 in the illustrated embodiment.

The CPMS 102 may be configured to communicate with the HBD 154, the authorized PMAD (402 of FIG. 4), and other facilities 316 across the internet 318, telecom network 314, or similar communication networks. In other embodiments, the CPMS 102 may be able to communicate with other devices within a healthcare home area network that is limited to communication within the proximity activation border 206.

Communication among the devices preferably employs strong encryption keys and remote access controls for devices that are paired to recognize each other, allowing a secure connection among the devices. The devices configured to operate within the proximity activation border 206 may be designed to close communication when one or both of the paired devices are not within the proximity activation border 206. Attempts to breach any of the devices, or changes in the patient's condition or the physical environment that may indicate unsafe conditions may be reported to the CPMS 102, other facilities 316, the HBD 154, the PMAD 402, emergency services (not pictured), or any other device or facility that comprises a part of the system.

The HBD 154 may be installed in a patient's home, a hospital room, an assisted living rehab/hospice room, or any other location where a patient may currently reside. The HBD 154 may not require that it be visible to anyone in the home or the room. The HBD 154 may be required to be placed in a location where the PMAD (402 of FIG. 4) may be able to communicate with the HBD 154.

Once installed, the HBD 154 may act as simple wireless base transmitter communicating unique IP address and MAC address information. The range of the HBD 154 transmitter may be configured to extend to a selected physical proximity, represented by the proximity activation border 206.

The HBD 154 may be configured to only communicate with three devices: the PMAD (402 of FIG. 4), the medical assistive devices 304 (including the environment sensors 306), and the CPMS 102. This may help to prevent other devices from accessing a patient's confidential information.

The HBD 154 may further be configured to include limited audio capabilities. The audio capabilities may be able to play pre-programmed terms or phrases that may signify that the patient should take an action. For example, a term or phrase may signify that the patient needs to have a banana to increase potassium. The terms or phrases may be selected with a purpose towards discreteness. For example, the device may suggest a banana for snack that does not disclose why that particular snack was suggested, where the patient may be aware of their condition that initiates the term or phrase. There may be other discrete programming terms or phrases for reminders to take medication that do not use the word medication. There may also be discreet reminders about taking in fluids that may be casual enough and nondirective enough to help the patient remember to have a glass of water. The terms or phrases may be programmed to signify almost any reminder, including to eat a meal, to drink water, to take a rest break, to go to the bathroom, take a bath, and to change clothes.

The HBD 154 may further be configured to alert the patient or healthcare provider to changes in conditions in a discreet way. The alert may be transmitted to any device or multiple devices within the proximity activation border 206 of the HBD 154 that may wirelessly communicate with the HBD 154. In one embodiment, the alert may be transmitted to a cell phone or smart phone 308 containing an app that will alert in a discreet way that may not disclose any sensitive information. The cell phone or smart phone 308 may display terms, phrases, or other information related to the alert, allowing the patient or the homecare provider to take appropriate action.

The CMPS 102 may be a centralized fixed computing device that receives requests from physicians or their designees to assign treatment for patients to be provided by healthcare providers. In one embodiment, the CPMS 102 may be configured to communicate with the HBD 154, the PMAD (402 of FIG. 4), or other facilities 316. The CPMS may connect through the internet 318 or telecom network 314, among other connection types capable of providing real-time or near real-time communication, such that a physician may communicate with the healthcare provider in real-time or near real-time while the healthcare provider is with the patient.

The PMAD (402 of FIG. 4) may comprise a smart phone 308, a laptop 310, a tablet 302, or any other device 312 which may maintain communication links with the HBD 154 or the CPMS 102, or both. In one embodiment, the PMAD (402 of FIG. 4) may be further configured to maintain communication links with medical assistive devices 304, which may comprise environment sensors 306.

The PMAD (402 of FIG. 4) may be issued to a healthcare provider or any other user assigned a service to perform for a patient. The PMAD (402 of FIG. 4) may contain the physician designation code; the medical service code(s) for the care to be provided by the physician, and turn-by-turn directions to the patient's location, such that the healthcare provider may know what procedure she is providing to the patient and where the patient resides. The address may not be displayed on the PMAD (402 of FIG. 4). The salutation and the patient's last name may be provided on the PMAD (402 of FIG. 4).

When turned on, the healthcare provider, or other user issued the PMAD (402 of FIG. 4), may enter a code for a new patient and a designation generated for the patient to trigger a download of information associated with the patient to the PMAD (402 of FIG. 4). The PMAD (402 of FIG. 4) may display a first portion of the downloaded information when the PMAD is located at any location. The first portion of the downloaded information may include turn-by-turn directions to the patient's location, the salutation of the patient, and the patient's last name.

The PMAD (402 of FIG. 4) may be configured to display a second portion of the downloaded information only when the PMAD (402 of FIG. 4) is within the proximity activation border 206. In one embodiment, an access code may be required to be entered into the PMAD (402 of FIG. 4) before the second portion of the downloaded information may be displayed. The second portion of the downloaded information may comprise any information necessary for the healthcare provider, or other user, to complete the assigned service for the patient.

The PMAD (402 of FIG. 4) may be configured with a wireless feature. The wireless feature may be networked with other medical devices to collect data and record data in a passive fashion while health care provider is making input. The collected and recorded data may be provided by the medical assistive devices 304, the environment sensors 306, or the HBD 154, among any other device that may collect data and may be configured to communicate data wirelessly.

The PMAD (402 of FIG. 4) may open an ATM connection or encrypted path to the CPMS 102 or the other facilities 316, which may include medical facilities, doctor's offices, hospitals, hospice care, nursing homes, and any other facility that may comprise a part of the system, alerting them that the healthcare provider is with a patient. The PMAD (402 of FIG. 4) may also communicate contact information for the healthcare provider (video conferencing, text, IM, e-mail or cell phone number) across the ATM connection or encrypted path. This may allow the physician, or other authorized personnel, to communicate with the healthcare provider while she is with the patient.

The medical assistive devices 304 may link to the HBD 154 when within the healthcare home area network, which the range of the network extends to the proximity activation border 206. The medical assistive devices 304 may collect diagnostic information on patients, including while the patients are not in the presence of a physician, healthcare provider, or other authorized personnel. The medical assistive devices 304 may include insulin pumps, diagnostic devices, blood pressure detection devices, temperature registering devices, or applications and diabetes management technology. The medical assistive devices may further comprise new medical assistive technologies like readings from home exercise technology, pulse and heart monitoring devices, motion detectors, room temperature registers, environment sensors 306, and any other type of device that may collect diagnostic information on patients or their surroundings.

In one embodiment, devices that report physiological states of a patient may be disengaged for a short period of time, allowing a patient to have privacy from the data collection. These devices comprise the environment sensors 306 and the medical assistive devices 304. In a further embodiment, notations may be provided to the CPMS by any of the devices within the proximity activation border 206.

FIG. 4 is an exemplary block diagram illustrating data communication between a CPMS 102, a PMAD 402, and a HBD 154. Communication may occur among the CPMS 102, the PMAD 402, and the HBD 154, as illustrated by the broken lines in 400.

Block 404 illustrates properties of the PMAD 402 and information that may be stored by the PMAD 402. The PMAD 408 may store patient IDs and medical files. In further embodiments, the PMAD 408 may store a physician designation code, a medical service code(s) for the care to be provided by the homecare provider, turn-by-turn directions to the patient's location, a salutation for the patient, and the patient's last name. The PMAD 408 may also store encrypted data on a healthcare provider's assignment for an entire day. Further, the PMAD 408 may store one or more records on unique patients including the patient's health information related to the treatment the healthcare provider should provide, treatments, medical services the healthcare provider should provide and test or report data the healthcare provider or the wireless features of the PMAD 408 should collect. In some embodiments, the PMAD 408 may be configured with a wireless component and geo-location control.

Block 406 illustrates properties of the HBD 154 and some types of information that may be stored by the HBD 154. The HBD 154 may operate as data storage. The HBD 154 may be configured with proximity detection and pairing, interface medical assistive devices 304, data collection, environmental monitoring, bed sensors, and the ability to contact emergency. The HBD 154 may be able to alert healthcare providers of serious or life threatening situations associated with a patient and relay information in near real-time through a secure encrypted communication link to the CPMS 102, such that a patient may obtain emergency care even when she is not in a situation to contact emergency services.

Figure 5:
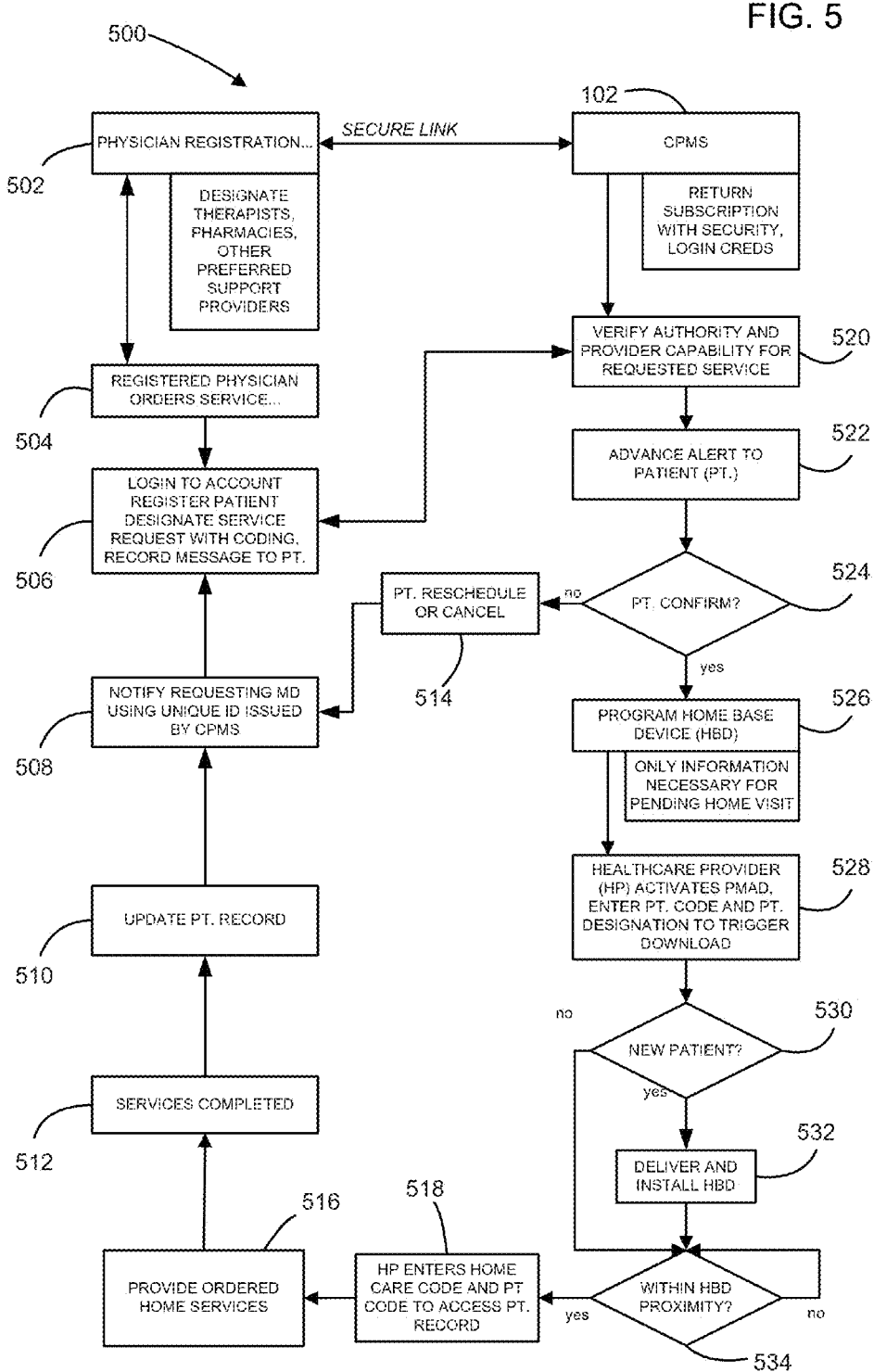
FIG. 5 is an exemplary flow chart illustrating operation of a secure healthcare management service.

FIG. 5 is an exemplary flow chart illustrating operation of a secure healthcare management service. A secure communication link may exist among the CPMS 102 and a physical or medical facility. The secure communication link may allow a physical or medical facility to receive reports from the CPMS 102.

A physician or other authorized medical personnel (collectively referred to as 'physician') may use the secure communication link to perform physician registration 502 with the CPMS 102. The physician may designate therapists, pharmacies, and other preferred medical support professionals that they may use to assist patients. In response to registration 502, the CPMS 102 may send a subscription to the physician's office. The subscription may be controlled by security protocols to assure that information is received by an authorized person in the physician's office.

In step 504, a physician registered with the CPMS 102 may order service for a patient. The process of ordering service may comprise the selecting of a healthcare provider to perform the desired service for the patient.

The physician completes the steps comprising step 506 to order service for the patient. The physician will log on to their account with the CPMS 102. The physician may register a patient for care, designate the type of service needed, and provide other details. A medical physician coding system may be used by the system to assure that patient and treatment instructions are clear. The physician may also record a message that may be used to alert the patient in advance of the appointment.

The request for service and other designated information may be transmitted to the selected healthcare provider. In step 520, the healthcare provider may verify the authority of the physician ordering the service and/or the healthcare provider's capability to perform the requested service. If the healthcare provider determines that the physician ordering the service does not have authority to do so or that the healthcare provider is unable to perform the requested service, the process may revert back to step 506 where the physician will be required to repeat the process of ordering service with a different healthcare provider selected. Otherwise, the process may continue to step 522.

In step 522, prior to the medical service provider's visit, a recorded message from the physician's office may be received by the patient alerting them to the pending visit by the healthcare provider, when the healthcare provider will arrive, and providing a call back number for the healthcare provider. The message may include the name of the healthcare provider and the entity the healthcare provider will be representing, as well as the physician's or medical facility's name and contact information.

The HBD 154 may alert the patient with the message and a physical indicator that the patient should expect a healthcare visit. In response to the alert of a pending visit by the healthcare provider, the patient may cancel, request rescheduling or confirm the appointment, shown in step 524.

If the appointment is cancelled or a rescheduling appointment request is initiated, shown in step 514, the physician may be alerted using a unique patient medical record designation generated by the CPMS 102, shown in step 508. The patient's request may be communicated to the physician through a message that may only contain the unique patient identifier generated by the CPMS 102. The physician may be required to access their account on the CPMS 102 to see the details of the patient request to protect the confidentiality of the patient's information.

If the patient confirms the appointment, or does not object or cancel the appointment, the HBD 154 may be programmed by the CPMS 102 with only the amount and type of information needed for the pending healthcare visit in step 526, limiting the amount of information that may be obtained outside of the medical facility setting. The HBD 154 may have a program control that requires a complete wipe (overwriting the information sufficiently to assure the data may not be recovered) before it can be reassigned to a new patient. Once the HBD 154 is programmed, the healthcare provider may take it to the residence of the patient, or other intended location of installation.

The healthcare provider may have a PMAD 404 with enabled wireless networking capability. In step 528, the healthcare provider may turn on the PMAD 404 and enter a patient code and patient designation, which may trigger the download of information associated with that patient and the service to be provided from the CPMS 102. The downloaded information may contain directions to the patient's residence and instructions concerning the service to be provided.

In step 530, it is determined whether the patient is a new patient. If the patient is a new patient, the flow continues to step 532. If not, the flow continues to step 534.

In step 532, the HBD 154 may be delivered and installed. The HBD 154 may be installed anywhere in the patient's residence that may allow communication between the HBD 154 and the PMAD 402. The HBD 154 may operate as a simple wireless base transmitter, with a selected limited range, communicating a unique IP address and MAC address information.

The HBD 154 may initialize by communicating with the CPMS 102 about its state to activate and run in a fixed geographic location. Once initialized, the HBD 154 may function in only two fixed geographic locations, the location of the CPMS 102 and the fixed geographic location where the HBD 154 was initialized. Once installed and initialized, the HBD 154 may only be reset by bringing the HBD 154 back to a management device (not shown), thereby ensuring that the HBD 154 is not transferred to a different location while maintaining the original patient's confidential information on the HBD 154.

In step 532, it is determined whether the PMAD 402 is within the proximity activation border 206 of the HBD 154. If the PMAD 402 is within the proximity activation border 206, the flow will continue to step 518. If not, the flow will remain in step 534 until the condition is satisfied.

In step 518, the healthcare provider may enter an access code into the PMAD 402 and a medical service record associated with the base device, the portion of the patient's medical record associated with the procedure stored on the PMAD 402, and other information stored on the PMAD 402 pertaining to the patient that were previously inaccessible may become accessible. For security of the confidential information of a patient, the PMAD 402 may be configured to allow access to medical records and information associated with only one patient at a time. Once a patient's medical record is accessed, the healthcare provider may need to complete the task for the patient or pause and close the session (which can be resumed later when the access code is reentered and the portable device is within the specified range of the base device) prior to accessing another patient's medical record.

In step 516, the healthcare provider performs the ordered services for the patient. Instructions for the service may be provided on the PMAD 402 to provide guidance to the healthcare provider on how to perform the service.

In step 512, the healthcare provider completes the services. The healthcare provider may complete the service by entering the required data for the service into the PMAD 402 and storing the data. To assure that a complete record is maintained over time, no deletion of data from the PMAD 402 may be performed.

In step 510, the patient's medical record is updated on the CPMS 102. The data stored on the PMAD 402 may be uploaded to the CPMS 102 at the end of the day, or at another scheduled time period. In order to protect the security of the transferred information, a secure communication link to transfer the data may be opened with the physician's office, hospital, nursing home, or hospice facility, if the facility has a device for this purpose. Alternatively, the data may be recorded in an account on the CPMS 102, which may send a message regarding updates or changes to the physician's office, hospital, nursing home, or hospice facility.

Once the data on the PMAD 402 is uploaded to the CPMS 102, the copy of the data remaining on the PMAD 402 may be deleted. The deletion may be made such that the data is unrecoverable. By making the data unrecoverable, the PMAD 402 may not be attractive for external threats to an attempt to breach nor to insider threats.

In step 508, notification may be provided to the physician requesting the service that the service has been completed, if the healthcare provider has completed the service and uploaded the data from the PMAD 402. Alternatively, if the patient requested rescheduling or cancellation of a scheduled healthcare appointment, the physician may be informed that the patient has made a request. By providing this notification the physician ordering the service may be aware of the progress or results of the ordered service shortly after information is uploaded to the CPMS 102.

Figure 6:
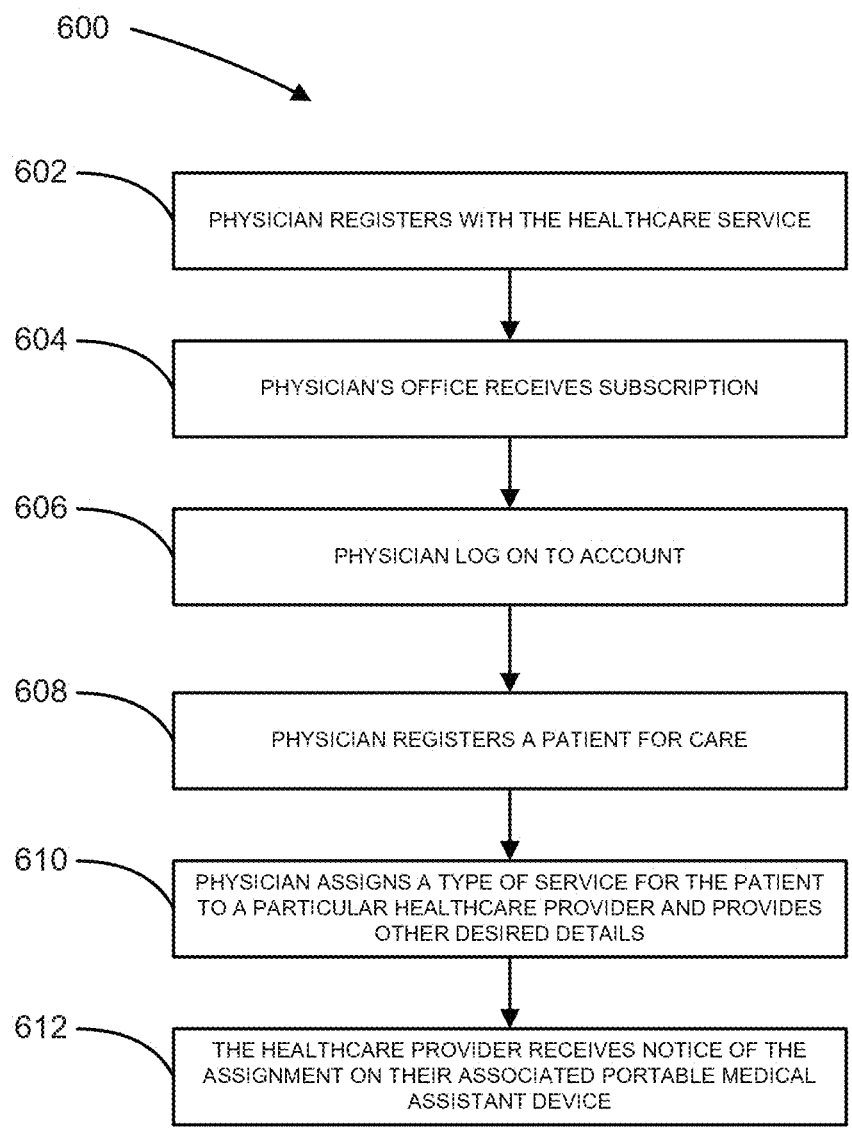
FIG. 6 is an exemplary flow chart illustrating a process for physician registration and assignment of services within a secure healthcare management service.

FIG. 6 is an exemplary flow chart illustrating a process for physician registration and assignment of services within a secure healthcare management service.

In step 602, the physician registers with the healthcare service establishing an account for the physician with the service. The physician may designate therapists, pharmacies, and/or other preferred medical support professionals, therein producing a list of healthcare providers from which the physician may select a healthcare provider to which to assign a service to be performed for a patient.

In step 604, the physician's office may receive a subscription from the healthcare service. The subscription may be controlled by security protocols to assure that the information is received by an authorized person in the physician's office.

In step 606, the physician may log on to the account using the subscription information provided in step 604. Once logged on to the healthcare service, the physician may be able to designate a service to be performed, update the list of healthcare providers, receive results of services performed by healthcare providers for patients, and receive requests to alter a healthcare provider visit schedule, among any other activities that the service may provide.

In step 608, the physician may register a patient for care provided by the service. Registering a patient for care may comprise designating the type of service to be performed for the patient and designating other details provided by the server, including which portion of a patient's medical record may be uploaded to the PMAD 402 to assist the healthcare provider in performing the service or instructions for performing the service. A medical physician coding system may be used by the service to assure that the type of service and associated instructions are clear.

In step 610, the physician may assign the service to be performed to a particular healthcare provider. The healthcare provider may be selected from the list of healthcare providers created upon registration with the system for ease of assignment by the physician. Alternatively, a healthcare provider not on the list of healthcare providers created upon registration with the system may be assigned the service and, further, the healthcare provider may be added to the list of healthcare providers stored on the server.

In step 612, a notice of the service assignment made by the physician may be provided to the PMAD 402 to inform the healthcare provider of the assignment. This notice may comprise details on the assigned service and instructions for completing the assigned service, such that the healthcare provider may verify his competence in performing the service. The notice may also comprise directions to the patient's location, and a salutation and surname of the patient such that the healthcare provider may determine the location of the patient and be able to address the patient when arriving at the patient's location.

Figure 7:
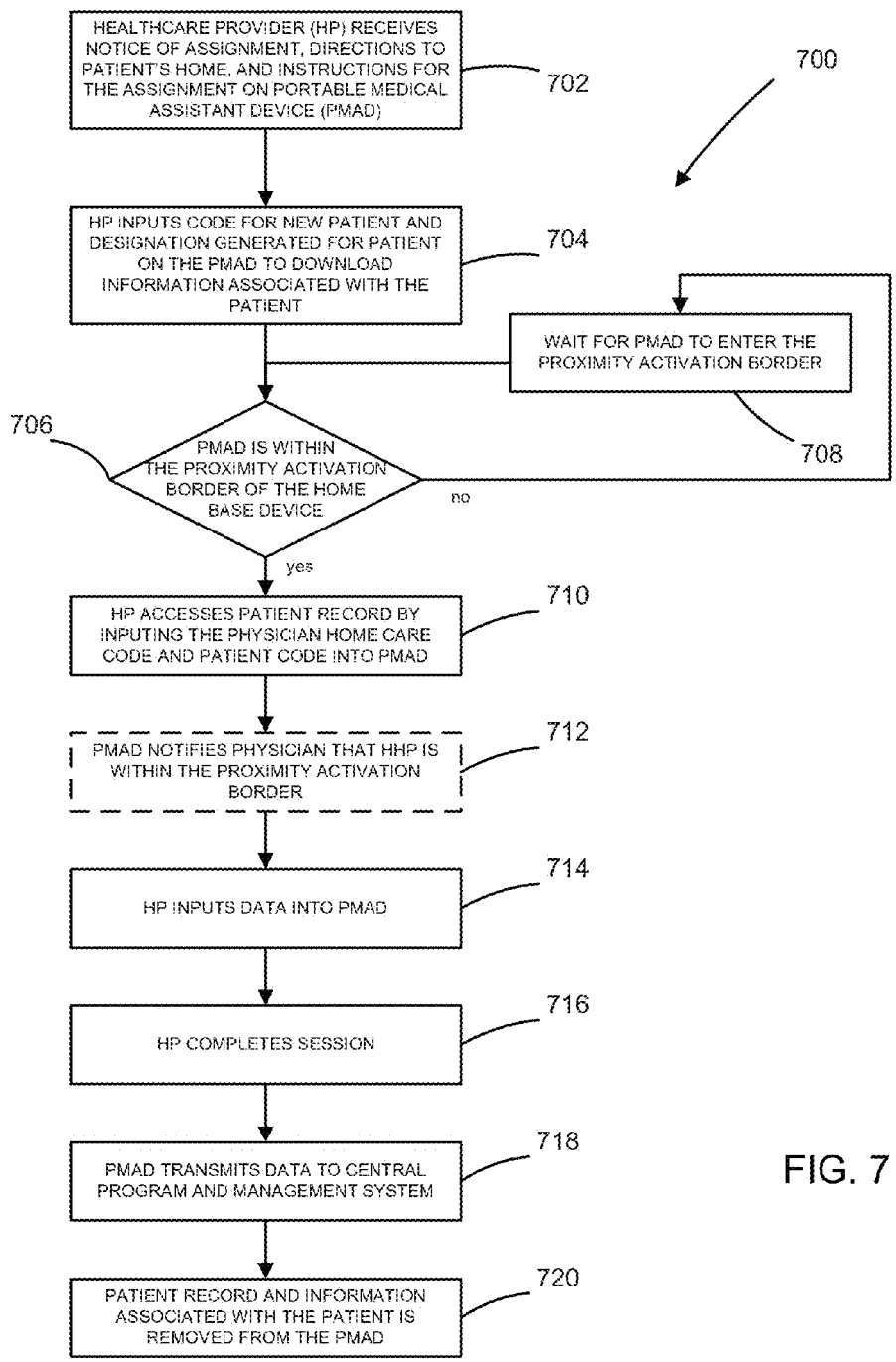
FIG. 7 is an exemplary flow chart illustrating operation of a portable medical assistant device by a healthcare professional.

FIG. 7 is an exemplary flow chart illustrating operation of a PMAD 402 by a healthcare professional. In step 702, the healthcare provider may receive notice of an assignment for service made by a physician on the PMAD 402. The notification may comprise directions to the patient's location. The directions may comprise turn-by-turn directions to the patient's location without providing an address for the patient's location, thereby allowing for the least amount of identifying information of the patient to be provided. The notification may comprise the patient's salutation and last name to assist the healthcare provider in communication with the patient. In addition, the notification may comprise details and instructions pertaining to the service for the patient, such that the healthcare provider may verify that the provider is able to perform the service. If the healthcare provider is unable to perform the service, the healthcare provider may send notification of such to the physician, thereby allowing the physician to assign the service to a different healthcare provider.

In step 704, the healthcare provider may input a code associated with the patient and a generated designation for the patient triggering the download of information associated with the patient and the assigned service. The input requirements may verify that the authorized healthcare provider is the only individual whom may download what may be confidential information to the PMAD 402. The information, or at least a portion of the information, downloaded to the PMAD 402 may not be accessible on the PMAD 402 until the system determines that the PMAD 402 is within the proximity activation border 206 of the HBD 154.

In step 706, the system may determine whether the PMAD 402 is within the proximity activation border 206. This determination may provide, possibly in combination with other criteria, the benefit of allowing a portion of the information on the PMAD 402 to be accessed within the proximity activation border 206. If the PMAD 402 is not within the proximity activation border 206, the flow may continue to step 708 where the system waits for the PMAD 402 to be within the proximity activation border 206 before the healthcare provider can continue with the service process. If the PMAD 402 is within the proximity activation border 206, the flow may continue to step 710.

In step 710, the healthcare provider may access the patient record, and any other information designated to only be accessible within the proximity activation border 206, by inputting the physician home care code and patient code into the PMAD 402. Inputting the codes into the PMAD 402 will allow the healthcare provider to access a portion of the information downloaded to the PMAD 402 in step 704 that was not previously accessible. This step may provide the additional security of verifying that the assigned healthcare provider is the only individual who may access the information.

If the PMAD 402 exits the proximity activation border 206 while information made accessible in step 710 is currently being accessed, the PMAD 402 may issue an alert and warning that the patient session is ending. The alert may be audible, such as to alert the healthcare provider that she is leaving the proximity activation border 206. For security of the patient's information, the warning and alert may not mention the name of the patient. If the PMAD 402 does not move back within the proximity activation border 206 within a short time of the warning, the HBD 154 and the PMAD 402 will close the link between the devices. Additionally, an auto log out command may be run on the PMAD 402, preventing the healthcare provider from accessing the information made accessible in step 710. The files being accessed when the PMAD 402 exits the proximity activation border 206 may be stored in a preliminary mode. After auto log out, when the PMAD 402 enters the proximity activation border 206 of any HBD 154, the PMAD 402 may display the unsaved data and provide the healthcare provider an opportunity to save the data. In order to view the unsaved data when within the proximity activation border 206, the healthcare provider may be required to input an initialization code and a joint authentication of an assigned patient's HBD 154. The PMAD 402 may be configured to not allow access or processing of another patient's data until the unsaved data is either saved or placed in a form hold.

Step 712 may provide the additional functionality of notifying the physician when the healthcare provider is within the proximity activation border 206. The notification may include contact information for the healthcare provider, comprising video conferencing, text messaging, instant messaging, e-mail, or cell phone number. The PMAD 402 may open an ATM connection or encrypted path to the physician or designated medical facility. Step 712 may allow the physician to communicate with healthcare provider while the healthcare provider is providing the service for the patient. The PMAD 402 may have audio and visual features that may alert the healthcare provider of communication from the physician or designated medical facility. The physician may access the medical service provider's visit and offer additional requests for further engagement with the patient. The physician's image may also be displayed on the PMAD 402 and the physician may be able to audibly communicate with the healthcare provider over the PMAD 402.

In step 714, the healthcare provider has completed the service and inputs the data produced during the service into the PMAD 402. To verify that the record of the service is complete, once data is input into the PMAD 402, the data may not be deleted. The data will be stored on the PMAD 402 until a connection is established with the CPMS 102 allowing the data to be uploaded to the CPMS 102. The upload may be scheduled to occur at certain times, at certain time intervals, or upon certain occurrences.

In step 716, the healthcare provider completes the session on the PMAD 402. The PMAD 402 may provide for confirmation by the healthcare provider prior to completion of the session, thereby allowing the healthcare provider to verify that all data associated with the service session has been entered into the PMAD 402 prior to upload of the information.

In step 718, the PMAD 402 transmits the input data to the CPMS 102. A secure communication link may be established between the PMAD 402 and the CPMS 102 to provide for maximum security of the patient's information. The input data may then be stored in an account on the CPMS 102 to be accessed by the physician. Alternatively, a secure communication link may be opened among the PMAD 402, the CPMS 102, and a designated medical facility allowing the data to be uploaded directly to a device at the medical facility.

In step 720, the patient record and any information associated with the patient is removed from the PMAD 402. For the security of the patient record and information, the record and information may be removed in such a way that it is unrecoverable. The record and information may be made unrecoverable by overwriting the data or any other technique now known or later developed that may make electronically stored data unrecoverable. The technique for making the data unrecoverable may be selected to be the technique that causes the least degradation or damage to a storage device.

Figure 8:
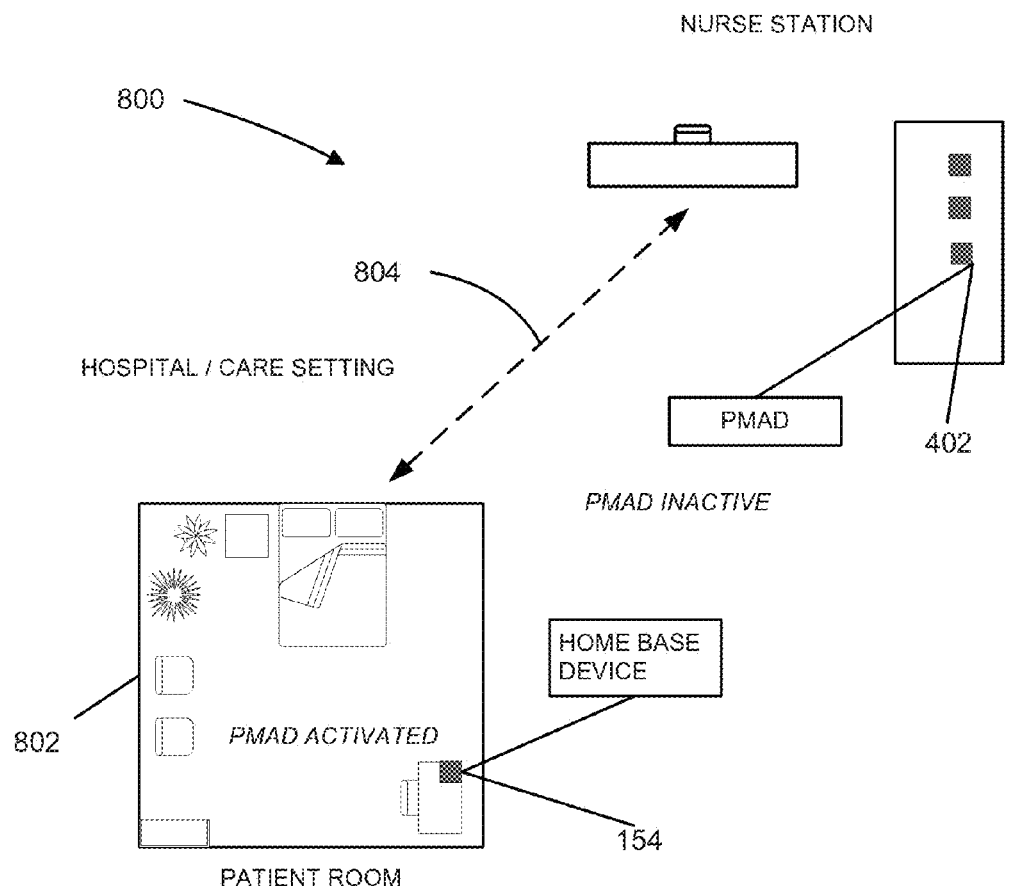
FIG. 8 illustrates use of a secure healthcare management system in a medical facility setting.

FIG. 8 illustrates use of a secure healthcare management system in a medical facility setting. As shown, the HBD 154 may be installed within a patient's room within a medical facility. The HBD 154 may be configured such that the proximity activation border 206 of the HBD 154 extends only to the borders of the patient's room 802, thereby allowing access to a portion of the information uploaded to the PMAD 402 to only be accessible within the patient's room.

The PMAD 402 may be stored in a location separate from the patient's room 802, such as by a nurse station as shown. A nurse, or other authorized healthcare provider, may then obtain the PMAD 402 from the storage location and use directions provided by the PMAD 402 to take the PMAD 402 to the patient's room 802 along a path 804 provided by the PMAD 402, allowing for the PMAD 402 to be activated within the patient's room 802. This setup may provide for greater security of the patient's information by making a portion of the information only accessible within the patient's room 802.

Figure 9:
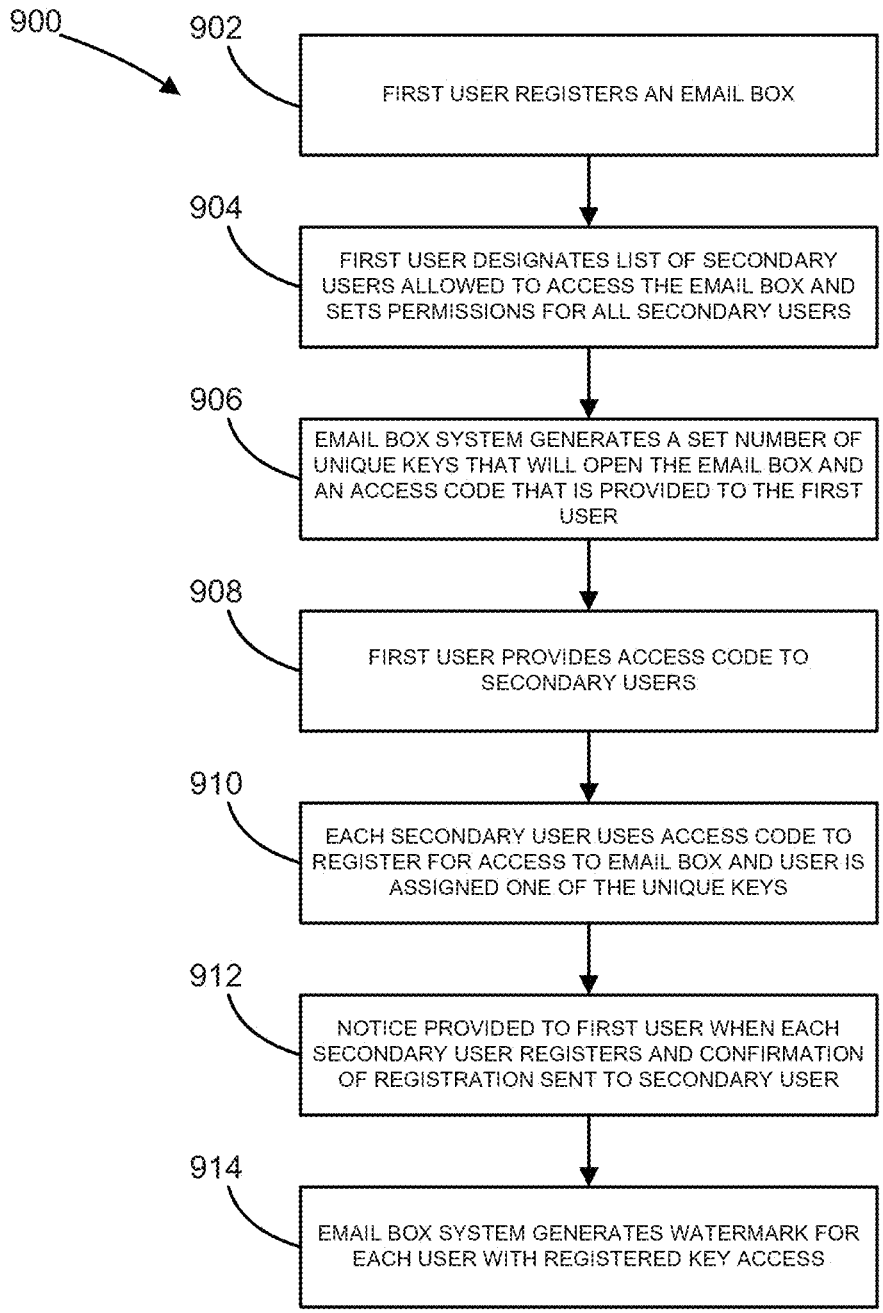
FIG. 9 is an exemplary flow chart illustrating setup of a secure email box provided by a healthcare service.

FIG. 9 is an exemplary flow chart illustrating setup of a secure email box provided by a healthcare service. The secure email box may provide for the secure transfer of data between users of the email box system. The users of the email box system may comprise physicians, patients, and/or healthcare providers. In one embodiment, the physician may act as a first user registering the secure email box and the physician may designate patients and/or healthcare providers as secondary users, allowing the secondary users access to the secure email box.

The secure email box may feature voice and video conferencing, notes, messages, reminders, and appointments, among other communication methods. The communications across the email box system may utilize 128-bit encryption or better. Due to the high levels of security and the real-time communication available through the secure email box system, the system may be ideal for transfer of confidential documents, such as a patient's medical records, among the physician, the patient, and the healthcare providers.

In step 902, a first user registers an email box. The first user may establish a network among multiple users to share data. The first user may be required to create a password key and a question with a secret answer that may provide further security to access of the email box.

In step 904, the first user may designate a list of secondary users allowed to access the email box. This may allow the first user to initially limit the users that may view any data placed into the email box. Additionally, the first user may set permissions for each secondary user. The permissions may comprise ability to read data placed in the email box, ability to write data to the email box, and the ability to modify data placed in the email box by other users.

In step 906, the email system may generate a set number of unique keys that may open the email box. The number of unique keys generated may be based on the number requested by the first user, thereby providing only access to the users that the first user provides the keys to. The first user may be assigned one of the unique keys and secondary users designated by the first user may each be assigned one of the other unique keys. The unique keys may be geo-location-linked and device-linked to maximize security. The unique keys may be stored on a portable device, comprising a thumb drive, a laptop, or any other portable device now known or later developed. Further, the email system may require the first user to create an access code, which may be distributed to the secondary users along with the unique keys as further security that only intended secondary users receive access to the email box.

In step 908, the first user provides the access code to the secondary users. The access code may be required in the process of the secondary users in setting up each secondary user's individual account.

In step 910, each secondary user uses the access code to register for access to the email box. By entering the access code, the secondary user verifies that the secondary user was intended to be granted access to the email box. Upon entry of the access code, the secondary user may be greeted by a welcome message requesting that the secondary user answer a question correctly before being granted access to the email box. The secondary user may also be assigned one of the unique keys generated by the email box system along with a log in.

In step 912, notice is provided to the first user when each secondary user registers an account. This may provide the first user with knowledge of who may currently access data on the email server. Additionally, confirmation of registration may be sent to the secondary user registering an email box account.

In step 914, the email box system may generate a watermark for each user with registered key access. The watermark may be used to signify which user posted which data to the email box.

Figure 10:
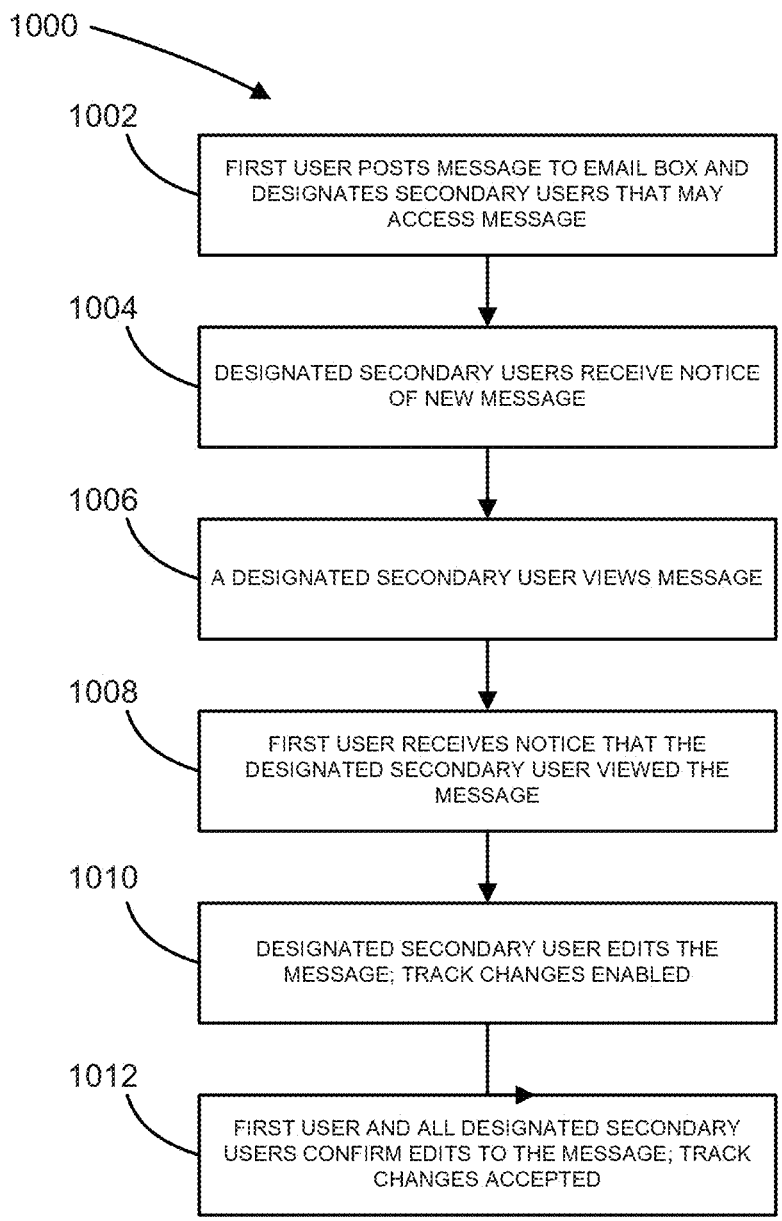
FIG. 10 is an exemplary flow chart illustrating message posting and editing on a secure email box.

FIG. 10 is an exemplary flow chart illustrating message posting and editing on a secure email box. The example illustrates functionality that the email box system may possess when a first user posts a message in the email box.

In step 1002, a first user posts a message to the email box. The first user may designate secondary users that may access the message. The ability to designate which secondary users may access the message allows the first user to exclude secondary users from seeing the message, thereby providing security to the information within the message. Once a message has been posted, the message may be configured such that no additional secondary users may be designated to access the message unless all users designated to view the message at the time of proposal of the additional secondary user agree that the additional secondary user may be designated to view the message.

In step 1004, the designated secondary users may receive notice of the new message posted by the first user. This provides the secondary users with knowledge of any new messages that may be posted.

In step 1006, a designated secondary user may view the message. The secondary user may access the message by accessing the secondary user's individual email box using the secondary user's pass code. The email box may store the digital signature of all users who have accessed the message. The message may be watermarked with the date and time stamps for users who have accessed the message as well as noting the location of the access.

In step 1008, the email box may be configured to provide notice to the first user when any secondary user views the message, thereby allowing the first user to verify that every secondary user required to view the message did so.

In step 1010, the designated secondary user may edit the message. Any edits to the message by the designated secondary user may be tracked and the tracking may associate the edits with the particular designated secondary user. This allows the first user and all other designated secondary users to view who made the edits to the message. Additionally, an edit to the message may comprise a reply to the message. Any replies to a message may create a new thread. The ability to edit messages may be utilized by a healthcare provider to edit a patient's medical record after completing service for a patient when if a physician posts the patient's medical record in the email box.

In step 1012, the first user and all designated secondary users may confirm the edits to the message. The confirmation process may begin with the user producing the edits confirming that the edits are a final draft. The message may then be updated to incorporate the edits as track changes. Each first user and designated secondary user may then affirm the edits. Once edits are affirmed by every user with access to the message, the track changes are removed from the message producing a new message incorporating the track changes.

Figure 11:
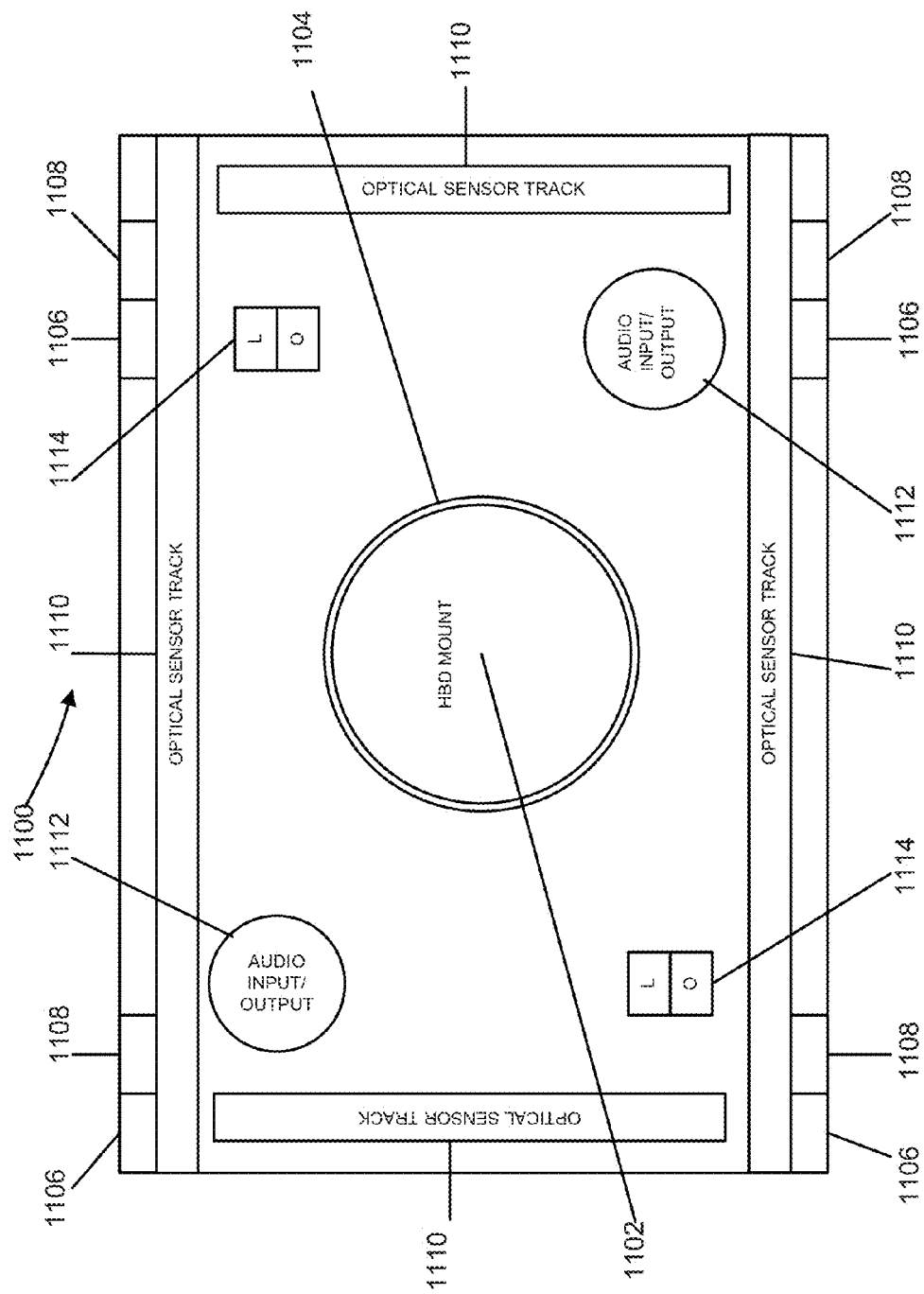
FIG. 11 is a top view of one example of a home base device cart layout.

FIG. 11 is a top view of one example of a home base device cart layout. The home base device cart 1100 may be used to allow the HBD 154 to become mobile within a specified area. The home base device cart 1100 may be configured such that the cart may remain within a selected range of a locator control device, thereby staying within the range of a patient's basic vocal commands. The locator control device may be worn by a patient and may comprise jewelry, a watch, a pendent, a necklace, a bracelet, or any other object that may be worn by a patient. The home base device cart 1100 may be configured to avoid the path of individuals within proximity to the cart and may be configured to move among locations that are hidden from sight.

The home base device cart 1100 may be configured with basic voice functions, such that the cart may communicate with a patient. Additionally, the home base device cart 1100 may be configured to receive basic verbal commands from a patient, including commands to contact emergency medical services. The ability to communicate with the patient and receive commands will help the home base device cart 1100 to better serve a patient by providing verbal reminders to a patient. The voice functions may also be configured to provide entertainment options for the patient, comprising jokes, music, news, digital books, and recorded speeches, among other types of audio entertainment.

The home base device cart 1100 may be configured to map locations where it may travel, either by input from a programmer or by learning the surrounding area. This will allow the home base device cart 1100 to be able determine paths of travel and obstacles. Particular locations on the map may be labeled, such as home, second floor, or yard. The home base device cart 1100 may be designed to for maximum silence, such that it will not disturb a patient.

The home base device cart 1100 may comprise a HBD mount 1102. The HBD mount 1102 may be configured to hold the HBD 154 and to communicatively couple the HBD 154 to the home base device cart 1100, such that the HBD 154 may utilize the features of the home base device cart 1100. The HBD 154 may be physically held in place by a lip 1104 that may be engaged using locking switch 1114. To prevent damage to the HBD 154 and home base device cart 1100 from elements, the lip 1104 may be designed to be watertight and resistant to spills.

The home base device cart 1100 may have optical sensor tracks 1110 along the edges of the top of the cart, such that the home base device cart 1100 may be able to identify objects above the cart helping the cart to find locations that are out of sight to stop. The optical sensor tracks 1110 may assist the home base device cart 1100 in mapping its physical surrounding. The optical sensor tracks 1110 may be used to determine which audio input/output, depending on intended direction of communication, should be utilized for optimal effect in communicating with the patient. The optical sensor tracks 1110 may be configured to identify obstacles and react quickly to identified obstacles, almost as a reflex, to avoid damage to the cart or obstacles. The obstacles may include animals, individuals, and the patient.

The home base device cart 1100 may have audio input/output 1112 used to communicate with the patient. The audio input/output 1112 may be accessed by the HBD 154, such that the HBD 154 may use the audio input/output 1112 to provide reminders to the patient. The audio input/output 1112 may be configured to receive basic commands from a patient, such that the home base device cart 1100 or the HBD 154 may respond to the commands. The audio input/output 1112 may also be configured to provide entertainment options for the patient, comprising jokes, music, news, digital books, and recorded speeches, among other types of audio entertainment. The audio input/output 1112 may be limited to warning tones when the home base device cart 1100 is in motion.

The home base device cart 1100 may comprise LEDs 1106. The LEDs 1106 may be configured to respond to the ambient light of the home base device cart's 1100 surroundings. In an embodiment, where the ambient light is low, such as at night, the LEDs 1106 may dim such that the home base device cart 1100 will still be visible, but will not prevent a patient from falling asleep. In an embodiment, where the ambient light is high, such as during the day, the LEDs 1106 may brighten such that a patient will be able to notice the cart. The LEDs 1106 may further be configured to fluctuate the intensity of light emitted, such as flashing, when the home base device cart 1100 is moving to help differentiate the LEDs 1106 from other light sources such that a patient will recognize the light is being emitted from the home base device cart 1100, making the patient aware of its presence. In an embodiment, the LEDs 1106 may be configured to dim when the home base device cart 1100 stops under a piece of furniture, or somewhere else that a patient or other individual is unlikely to travel, as there may be a lower chance of the home base device cart 1100 interfering with the patient moving around.

The home base device cart 1100 may comprise ambient light sensors 1108. The ambient light sensors 1108 may be configured to sense changes in ambient light that may signify issues that a patient may experience. In an embodiment, the ambient light sensors 1108 may sense lights being turned on in the middle of the night, showing that the patient is not sleeping through the night. The ambient light sensors 1108 may be communicatively coupled to the LEDs 1106, such that the LEDs 1106 may respond to changes in data obtained by the ambient light sensors 1108.

Figure 12:
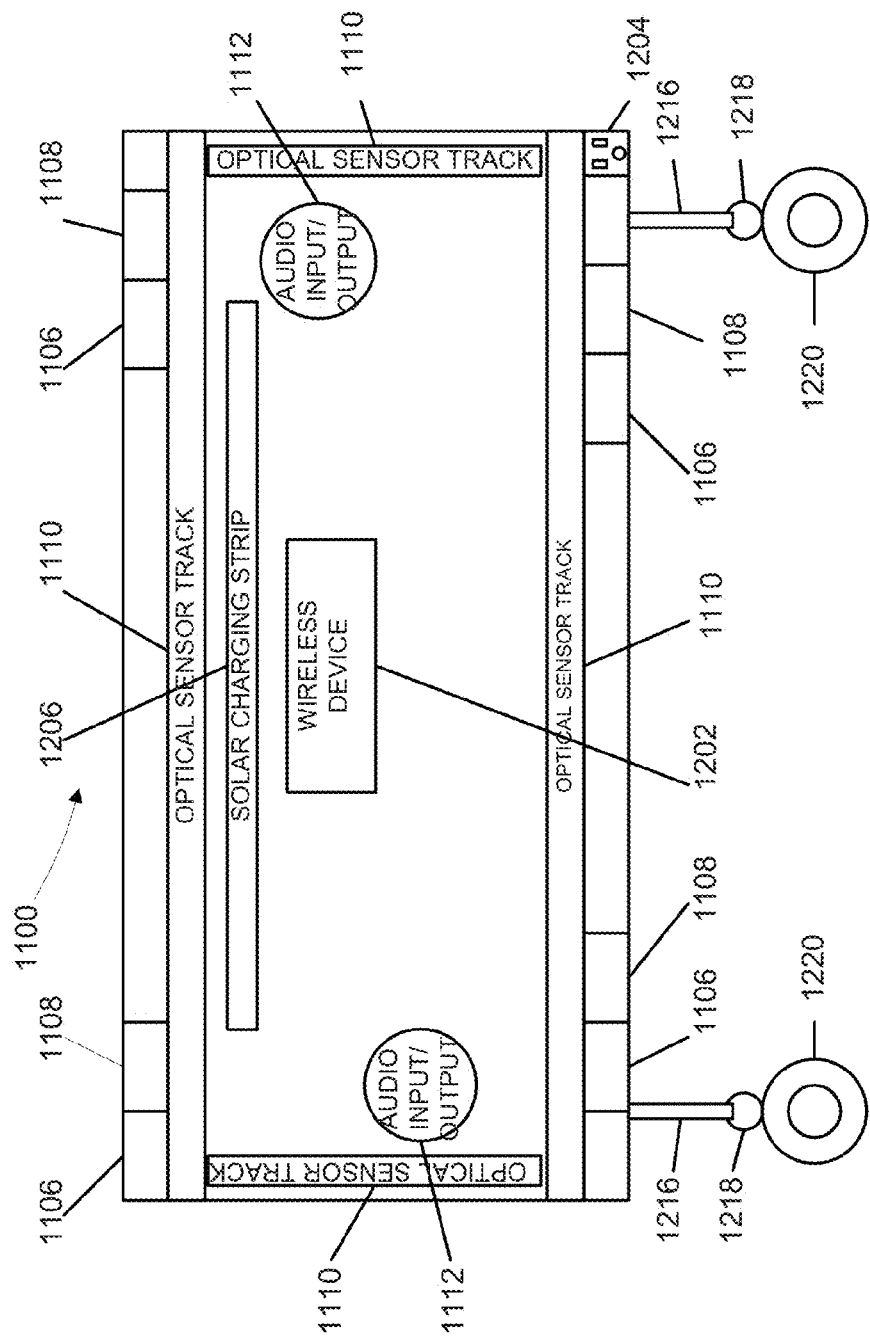
FIG. 12 is a side view of one example of a home base device cart layout.

FIG. 12 is a side view of one example of a home base device cart layout.

The home base device cart 1100 may be designed to operate for extended periods of time on limited battery life. The home base device cart 1100 may be configured to sound an audible low battery warning when battery charge drops below a certain level. Additionally, the features of the home base device cart 1100 may be configured to lose power when the battery charge drops below a second certain level, but power may be maintained to the HBD 154 such that it will still be able to operate. The home base device cart 1100 may have a wall charger 1204, such that the cart may be plugged into a wall outlet to charge. The home base device cart 1100 may have a solar charging strip 1206 such that the cart may utilize ambient light within a room or light from the sun for energy. The solar charging strip 1206 may comprise any existing light-based charging technology now known or later developed that may suit the conditions in which the home base device cart 1100 may operate.

The home base device cart 1100 may have optical sensor tracks 1110 along the edges of the top of the cart, such that the home base device cart 1100 may be able to identify objects above the cart helping the cart to find locations that are out of sight to stop. The optical sensor tracks 1110 may assist the home base device cart 1100 in mapping its physical surrounding. The optical sensor tracks 1110 may be used to determine which audio input/output, depending on intended direction of communication, should be utilized for optimal effect in communicating with the patient. The optical sensor tracks 1110 may be configured to identify obstacles and react quickly to identified obstacles, almost as a reflex, to avoid damage to the cart or obstacles.

The home base device cart 1100 may have audio input/output 1112 used to communicate with the patient. The audio input/output 1112 may be accessed by the HBD 154, such that the HBD 154 may use the audio input/output 1112 to provide reminders to the patient. The audio input/output 1112 may be configured to receive basic commands from a patient. The audio input/output 1112 may also be configured to provide entertainment options for the patient, comprising jokes, music, news, digital books, and recorded speeches, among other types of audio entertainment. The audio input/output 1112 may be limited to warning tones when the home base device cart 1100 is in motion.

The home base device cart 1100 may comprise LEDs 1106. The LEDs 1106 may be configured to respond to the ambient light of the home base device cart's 1100 surroundings. In an embodiment, where the ambient light is low, such as at night, the LEDs 1106 may dim such that the home base device cart 1100 will still be visible, but will not prevent a patient from falling asleep. In an embodiment, where the ambient light is high, such as during the day, the LEDs 1106 may brighten such that a patient will be able to notice the cart. The LEDs 1106 may further be configured to fluctuate the intensity of light emitted, such as flashing, when the home base device cart 1100 is moving to help differentiate the LEDs 1106 from other light sources such that a patient will recognize the light is being emitted from the home base device cart 1100, making the patient aware of its presence. In an embodiment, the LEDs 1106 may be configured to dim when the home base device cart 1100 stops under a piece of furniture, or somewhere else that a patient or other individual is unlikely to travel, as there may be a lower chance of the home base device cart 1100 interfering with the patient moving around.

The home base device cart 1100 may comprise ambient light sensors 1108. The ambient light sensors 1108 may be configured to sense changes in ambient light that may signify issues that a patient may experience. In an embodiment, the ambient light sensors 1108 may sense lights being turned on in the middle of the night, showing that the patient is not sleeping through the night. The ambient light sensors 1108 may be communicatively coupled to the LEDs 1106, such that the LEDs 1106 may respond to changes in data obtained by the ambient light sensors 1108.

The home base device cart 1100 may have tires 1220 for mobility. The tires 1220 may be heavy tread tires of solid construction, such that the tires may travel across all different types of surfaces and the tires may require minimal maintenance. The tires 1220 may be coupled to the main body of the home base device cart 1100 by legs 1216 and bearings 1218. The bearings 1218 may be configured to move independent to each other bearing on the cart and allow for maximum rotation angles for optimal range of mobility. The home base device cart 1100 may be configured to adjust height of the unit and move on two wheels in a stable manner to circumvent obstacles.

The home base device cart 1100 may comprise a wireless device 1202. The wireless device 1202 may be used to locate the home base device cart 1100 in the event of an emergency. The home base device cart 1100 may contact emergency services and transmit its location, such as a beacon, to the emergency services, such that the emergency services will be able to determine the location of the patient and provide the patient care in the situation where the patient may not be able to contact emergency services on her own. For example, diabetics and Alzheimer's patients with diminished capacity medical conditions may be in a state where they are not fully in control of their actions and the home base device cart 1100 may be able to contact emergency services to obtain care for the patient. In an embodiment, if the home base device cart 1100 should cease to function, the HBD 154 may operate as a beacon signifying the patient's location. The wireless function may be limited to an emergency beacon or to tap into GPS services to navigate back to a home base or alert in the event that it moves beyond a point that may indicate that the patient may be in crisis or about to enter crisis.

In an embodiment, the wireless device 1202 may be used to locate a recharging location, such that the home base device cart 1100 may travel to the recharging location to wirelessly recharge its battery. The recharging location may be within a proximity to a table recharging station or a floor recharging station, among other recharging technologies that may be utilized by the home base device cart 1100.

It will be apparent to those having skill in the art that many changes may be made to the details of the above-described examples without departing from the underlying principles of the invention. The scope of the present invention should, therefore, be determined only by the following claims.

Most of the equipment discussed above comprises hardware and associated software. For example, the typical portable device is likely to include one or more processors and software executable on those processors to carry out the operations described. We use the term software herein in its commonly understood sense to refer to programs or routines (subroutines, objects, plug-ins, etc.), as well as data, usable by a machine or processor. As is well known, computer programs generally comprise instructions that are stored in machine-readable or computer-readable storage media. Some embodiments of the present invention may include executable programs or instructions that are stored in machine-readable or computer-readable storage media, such as a digital memory. We do not imply that a "computer" in the conventional sense is required in any particular embodiment. For example, various processors, embedded or otherwise, may be used in equipment such as the components described herein.

Memory for storing software again is well known. In some embodiments, memory associated with a given processor may be stored in the same physical device as the processor ("on-board" memory); for example, RAM or FLASH memory disposed within an integrated circuit microprocessor or the like. In other examples, the memory comprises an independent device, such as an external disk drive, storage array, or portable FLASH key fob. In such cases, the memory becomes "associated" with the digital processor when the two are operatively coupled together, or in communication with each other, for example by an I/O port, network connection, etc. such that the processor can read a file stored on the memory. Associated memory may be "read only" by design (ROM) or by virtue of permission settings, or not. Other examples include but are not limited to WORM, EPROM, EEPROM, FLASH, etc. Those technologies often are implemented in solid state semiconductor devices. Other memories may comprise moving parts, such as a conventional rotating disk drive. All such memories are "machine readable" or "computer-readable" and may be used to store executable instructions for implementing the functions described herein.

A "software product" refers to a memory device in which a series of executable instructions are stored in a machine-readable form so that a suitable machine or processor, with appropriate access to the software product, can execute the instructions to carry out a process implemented by the instructions. Software products are sometimes used to distribute software. Any type of machine-readable memory, including without limitation those summarized above, may be used to make a software product. That said, it is also known that software can be distributed via electronic transmission ("download"), in which case there typically will be a corresponding software product at the transmitting end of the transmission, or the receiving end, or both.

Having described and illustrated the principles of the invention in a preferred embodiment thereof, it should be apparent that the invention may be modified in arrangement and detail without departing from such principles. We claim all modifications and variations coming within the spirit and scope of the following claims.

The invention claimed is:

1. A healthcare system comprising:
(A) a central server, (B) a home base device (HBD), and (C) a portable medical assistant device (PMAD);
the central server configured to—
communicate with selected medical facilities, healthcare providers, the portable medical assistant device (PMAD), and the home base device (HBD);
login a registered physician or her designee to enable the registered physician or her designee to schedule a specific procedure to be provided to a specific patient at a geographic location associated with the patient in the central server;
store data at the server comprising the scheduled specific procedure;
identify a PMAD associated in the central server with a healthcare provider that is designated to provide services including the specific procedure;
download first information specifying at least the patient, the procedure, and the geographic location, to the portable medical assistant device (PMAD),
download second information, including selected private medical records of the patient that are pertinent to the specific procedure, to the PMAD;
communicate with an HBD, including receiving indicia of a current location of the HBD;
determine from the indicia whether the HDB is located at the geographic location; and
if the HBD is located at the geographic location, initialize—activate the HBD for operation at the geographic location;
the home base device (HBD) configured to—
communicate with the central server, including sending indicia of a current location of the HBD to the central server;
receive an initialization instruction from the central server;
responsive to receiving the initialization instruction, condition further communications with the HBD to function only while the HBD remains at the current location or at a second location proximate to the central server;
determine whether the PMAD is located within a proximity activation border of the current location of the HBD;
responsive to a determination that the PMAD is located within the proximity activation border, communicate with the portable medical assistant device (PMAD) to cause the PMAD to release access to the second information; and
the portable medical assistant device (PMAD) configured to—
login an authorized user;
receive a patient code input from the user;
responsive to the patient code corresponding to the first information downloaded from the central server, enable user access to the first information;
determine whether the PMAD is located within a proximity activation border of the HBD;
receive a communication from the HBD to enable release;
conditioned on both a determination that the PMAD is located within the proximity activation border and receipt of the communication from the HBD, enable user access to the second information.

2. The system of claim 1, wherein the portable medical assistant device (PMAD) is further configurable to acquire and store diagnostic information from the home base device (HBD) while the PMAD is located within the proximity activation border.

3. The system of claim 1, wherein the PMAD is configured to lock itself when it is out of range of the home base device, so as to prevent disclosure of patient information stored in the PMAD.

4. The system of claim 1, wherein the PMAD is configured to communicate an alert to the central server responsive to an unauthorized attempt to access patient data stored on the PMAD.

5. The system of claim 1, wherein the central server is configured to enable a registered physician to populate a list of healthcare providers and to assign one of the healthcare providers from the list to perform the specific procedure for the specific patient at the geographic location.

6. The system of claim 5, wherein the PMAD is configured to enable the assigned healthcare provider to access a limited portion of the specific patient's health information, the limited portion selected as pertinent to the specific procedure assigned to the healthcare provider, the access enabled only while the PMAD is within the selected physical proximity to the home base device.

7. The system of claim 6, wherein the PMAD is configured to enable access to a second patient's information only after information input by the assigned healthcare provider associated with the first patient has been saved in the PMAD.

* * * * *